(12) United States Patent
Shtein et al.

(10) Patent No.: US 11,391,674 B2
(45) Date of Patent: Jul. 19, 2022

(54) BULK LIQUID TAGGING, IDENTIFYING AND AUTHENTICATION

(71) Applicant: Dotz Nano Ltd., Petach Tikva (IL)

(72) Inventors: Michael Shtein, Be'er Sheva (IL); Yoni Engel, Raanana (IL); Avigdor Kaner, Ramat Gan (IL); Yonit Boguslavsky, Petach Tikva (IL); Amit Haviv, Petach Tikva (IL)

(73) Assignee: Dotz Nano Ltd., Petah Tikva (IL)

( * ) Notice: Subject to any disclaimer, the term of this patent is extended or adjusted under 35 U.S.C. 154(b) by 254 days.

(21) Appl. No.: 16/608,075

(22) PCT Filed: Jun. 26, 2018

(86) PCT No.: PCT/US2018/039428
§ 371 (c)(1),
(2) Date: Oct. 24, 2019

(87) PCT Pub. No.: WO2018/201168
PCT Pub. Date: Nov. 1, 2018

(65) Prior Publication Data
US 2020/0072753 A1      Mar. 5, 2020

Related U.S. Application Data

(60) Provisional application No. 62/491,354, filed on Apr. 28, 2017.

(51) Int. Cl.
*G01N 21/64*      (2006.01)
*G01N 33/03*      (2006.01)
(Continued)

(52) U.S. Cl.
CPC ......... *G01N 21/6489* (2013.01); *G01N 33/03* (2013.01); *G01N 33/146* (2013.01); *G01N 33/2823* (2013.01)

(58) Field of Classification Search
CPC .. G01N 21/6489; G01N 33/03; G01N 33/146; G01N 33/2823; G01N 21/17; G01N 33/14; G01N 33/26
See application file for complete search history.

(56) References Cited

U.S. PATENT DOCUMENTS 7,712,528 B2 * 5/2010 Langdon ............... E21B 43/168
166/272.4
7,770,646 B2 * 8/2010 Klassen ................ E21B 43/243
166/303

(Continued)

FOREIGN PATENT DOCUMENTS

WO    WO-2014/063725 A1    5/2014

OTHER PUBLICATIONS

International Application No. PCT/US2018/039428, International Search Report and Written Opinion, dated Sep. 10, 2018.

*Primary Examiner* — Marcus H Taningco
(74) *Attorney, Agent, or Firm* — Marshall, Gerstein & Borun LLP

(57) ABSTRACT

The disclosure is directed to systems, compositions and methods for tagging, identifying and authenticating bulk liquids. Specifically, the disclosure relates to methods, compositions and systems for selectively and specifically identifying bulk liquids as authentic using, as a tagging compound, photoluminescent carbon nanostructures (PCN's) suspended in a continuous phase that is thermodynamically incompatible with non-polar bulk liquid and/or substantially low concentration of PCNs; and incorporating the suspension into the liquid, wherein the suspension is incorporated at a concentration of continuous phase that is at least one of being below the solubility limit of the suspension's continuous phase in the bulk liquid and a concentration that cannot be observed unaided to the naked eye.

10 Claims, 13 Drawing Sheets

(51) Int. Cl.
*G01N 33/14* (2006.01)
*G01N 33/28* (2006.01)

(56) References Cited

U.S. PATENT DOCUMENTS

| | | |
|---|---|---|
| 7,910,376 B2 | 3/2011 | Menzel |
| 9,528,045 B2 | 12/2016 | Kanj et al. |
| 2008/0138797 A1 | 6/2008 | Hunt et al. |
| 2010/0125035 A1* | 5/2010 | Zhang ............... B01J 21/185 |
| | | 502/180 |
| 2011/0214488 A1 | 9/2011 | Rose et al. |
| 2012/0034702 A1 | 2/2012 | Croud et al. |
| 2013/0109597 A1 | 5/2013 | Sarkar et al. |
| 2016/0371704 A1 | 12/2016 | Akgun et al. |

\* cited by examiner

BULK LIQUID TAGGING, IDENTIFYING AND AUTHENTICATION

BACKGROUND

The present disclosure relates to systems and methods for tagging and authenticating bulk liquids. Specifically, the disclosure relates to methods, compositions and systems for selectively and specifically identifying bulk liquids as authentic using photoluminescent carbon nanostructures (PCNs) suspended in a continuous phase that is thermodynamically incompatible with non-polar bulk liquid and/or substantially low concentration of PCNs in either non-polar or polar bulk liquids; and incorporating the suspension into the liquid, wherein the suspension is incorporated at a concentration of continuous phase that is at least one of being below the solubility limit of the suspension's continuous phase in the bulk liquid and a concentration that cannot be observed unaided to the naked eye that is sought to be, tagged, identified and authenticated.

The adulteration, counterfeiting, tampering, unauthorized distribution and sale of working bulk liquids has emerged as substantial problems for both manufacturers and governments alike. Likewise, in assigning culpability for major spills or leaks from pipelines. The foregoing has created circumstances where identifying the source of the bulk working liquids and authenticating the source is essential to maintain the integrity of the supply chain of these bulk working liquids.

Tagging has been requested by manufacturers, distributors and governments alike in order to mitigate the aforementioned issues. Tagging can be done by for example, adding a colorant, a fluorescent compound, or other easily detectable markers.

However, certain liquids, for example, petrol-based hydrocarbons have high absorption and/or fluorescence at exactly the same range most of the fluorescent tagging markers' emission, while use of metallic quantum dots (e.g., cadmium) may be toxic and not cost effective in bulk liquids such as wines and olive oils, with yet other markers being incompatible with the bulk working liquid sought to be tagged.

These and other aspects are addressed by the following systems compositions and methods.

SUMMARY

Disclosed, in various embodiments, are system, compositions and methods for selectively and specifically identifying bulk liquids as authentic by tagging these bulk working liquids using PCNs suspended in a continuous phase that can be thermodynamically incompatible with the bulk liquid sought to be tagged in non-polar bulk liquids, identified and authenticated.

In an embodiment, provided herein is a method of tagging a liquid, comprising: providing a composition comprising PCNs suspended in a continuous phase having at least one of a limited solubility in the tagged liquid and substantially low concentration of PCNs; and incorporating the suspension into the liquid, wherein the suspension is incorporated at a concentration of continuous phase that is at least one of being below the solubility limit of the suspension's continuous phase in the bulk liquid and a concentration that cannot be observed unaided to the naked eye.

In another embodiment, provided herein is a method of identifying a tagged liquid, implementable in a tagged liquid wherein the liquid was tagged by incorporating a composition comprising PCNs suspended in a continuous phase having limited solubility in the tagged liquid at a concentration of continuous phase that is below the solubility limit, the method comprising: obtaining a sample of predetermined volume from the bulk liquid; admixing into the bulk liquid the continuous phase of the suspension to a concentration above the solubility limit of the continuous phase in the tagged liquid; partitioning the continuous phase from the tagged liquid; and detecting the fluorescent emission spectra of the continuous phase.

In yet another embodiment, provided herein is a method of identifying a tagged liquid, implementable in a tagged liquid wherein the liquid was tagged by incorporating a composition comprising PCNs at a concentration of between 8 ppb and 999 ppm, wherein the PCNs have at least two discrete peak emission wavelength, the method comprising: obtaining a sample of predetermined volume from the bulk liquid; detecting the fluorescent emission spectra of the bulk liquid with the PCNs; and subtracting the fluorescent emission spectra of the bulk liquid without the PCNs.

In an embodiment, provided herein is a system for authenticating a bulk working liquid, the system comprising a display, a fluorescence detector; a bulk liquid container; and a processing unit coupled to the fluorescence detector, with a processing module comprising a processor in communication with a linked library containing original emission spectra of at least one of: a specific wavelength, excitation and emission contour map, and absorption spectra, of a tagging PCN incorporated in authentic liquid sought to be authenticated; the processor further being in communication with a non-volatile memory having thereon a processor-readable medium with a set of executable instructions configured to: receive a fluorescence reading from the fluorescence detector; retrieve from the linked library at least one of a predetermined emission spectra at a specific wavelength, excitation and emission contour map, and absorption spectra; and if at least one of the emission spectra at a specific wavelength, excitation and emission contour map, and absorption spectra, retrieved from the fluorescence detector correlates with at least one of the emission spectra at a specific wavelength, excitation and emission contour map, and absorption spectra, retrieved from the linked library, authenticating the tagged liquid; else identifying the liquid as non-authentic.

These and other features of the systems, compositions and methods for selectively and specifically selectively and specifically identifying bulk liquids as authentic using PCNs suspended in at least one of a continuous phase that is thermodynamically incompatible with bulk non-polar liquid sought to be tagged, and PCNs having at least two discrete peak emission wavelength at a concentration in the bulk liquid of between 8 ppb and 999 ppm identified and authenticated, will become apparent from the following detailed description when read in conjunction with the drawings, which are exemplary, not limiting.

BRIEF DESCRIPTION OF THE FIGURES

For a better understanding of the systems, compositions and methods, for tagging, identifying and authenticating bulk fluids with regard to the embodiments thereof, reference is made to the accompanying drawings, in which.

DESCRIPTION

Provided herein are embodiments of systems, compositions and methods for selectively and specifically identifying bulk liquids as authentic in a non-toxic, low cost manner, using PCNs suspended in a continuous phase that is thermodynamically incompatible with a non-polar bulk liquid sought to be, tagged, identified and authenticated and/or are present as a PCN combination having a plurality (two or more) of discrete peak emission wavelength at a concentration of between about 8 ppb and 999 ppm in any bulk liquid (polar or non-polar).

Bulk working fluids or liquids that can be tagged, identified and authenticated using the systems compositions and methods described herein can be, for example, petrol-derived hydrocarbon such as crude oil, petroleum fuels, kerosene, lubricating oils, or aqueous bulk liquids such as, for example, adBlue; as well as edible liquids such as wines, olive oils, palm oil (e.g. palmolein), balsamic vinegar, honey. These bulk fluids are characterized by having either a high background fluorescence, phosphorescence, chemiluminescence, or are sensitive to toxic markers, or which have a bulk cost that is low, making cost effectiveness of the tagging method a substantial factor. Furthermore, most are characterized by having a relatively homogeneous continuous phase.

The systems, compositions and methods provided herein can be used to tag, and/or identify and/or authenticate a bulk liquid, by incorporating PCNs, which are structured to be inert and non-toxic into the bulk liquid. The PCNs can be in a suspended system, for example in a suspension, gel, emulsion, duplex emulsion, duplex suspended system, or their combination, which will depend on the phase (or continuous phase) homogeneity of the bulk liquid sought to be tagged and/or identified, and/or authenticated.

As used herein, photoluminescent carbon nanostructures or PCNs can be, for example, nano-sized structures of carbon molecules (more than a single atom) having dimensionality that is anywhere from quasi-one dimension (e.g., quantum dot, nanoribbon, nanobelt), to three dimensional (e.g., multilayer graphene structures). Beyond these PCNs, also included in these nano-sized structures, are graphene, graphdiyne, fullerene, nanocage, multilayer graphene dot, nanodiamond, nanotube, nanowire, nanohorn, or a PCNs composition comprising one or more of the foregoing.

Figure 1A:
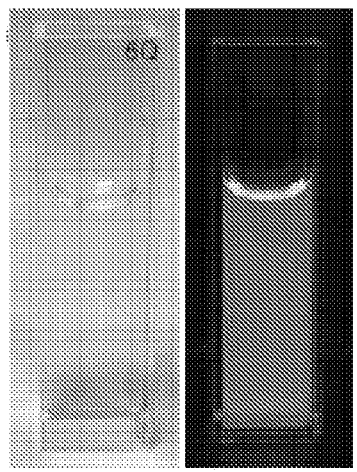
FIG. 1A, shows the luminescence characteristic of PCNs having a size emitting blue luminescence, with excitation and emission contour map illustrated in FIG. 1B, photoluminescence emission spectra at 350 nm excitation in FIG. 1C, and absorption spectra illustrated in FIG. 1D.
Figure 3A:
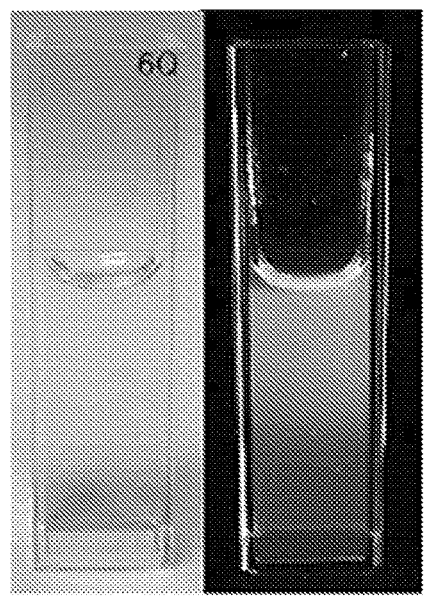
FIG. 3A, shows the luminescence characteristic of PCNs having a size emitting green luminescence, with excitation and emission contour map illustrated in FIG. 3B, photoluminescence emission spectra at 485 nm excitation in FIG. 3C, and absorption spectra illustrated in FIG. 3D.
Figure 12:
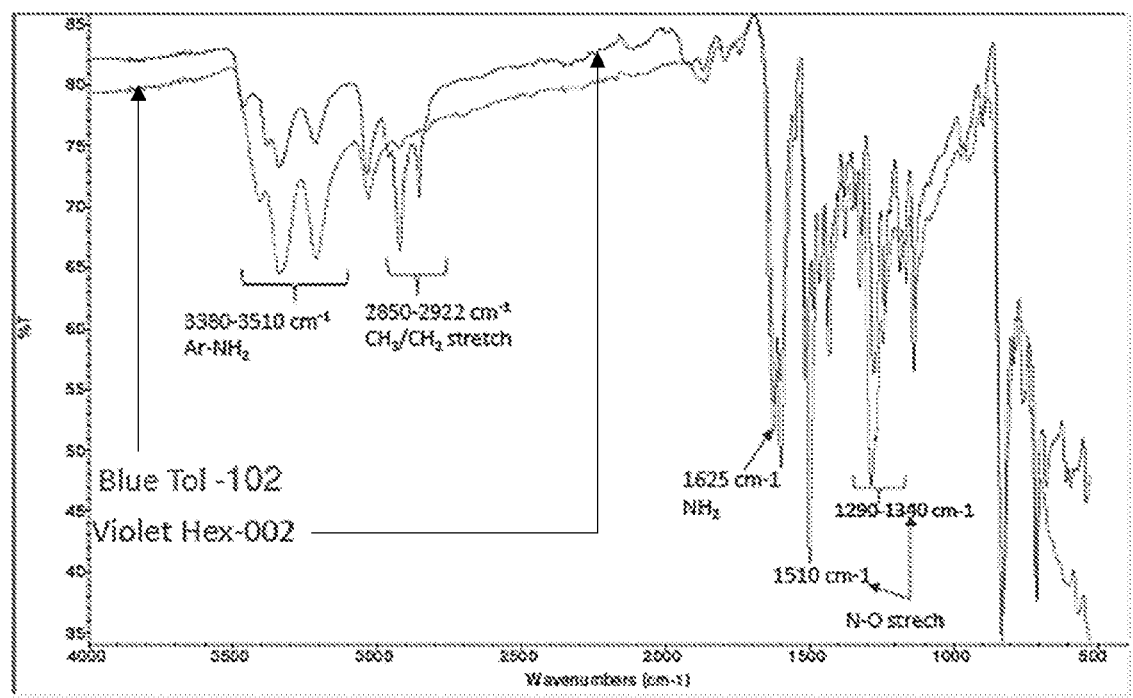
FIGS. 12-13, show FT-IR spectra comparison of various PCN used.
Figure 13:
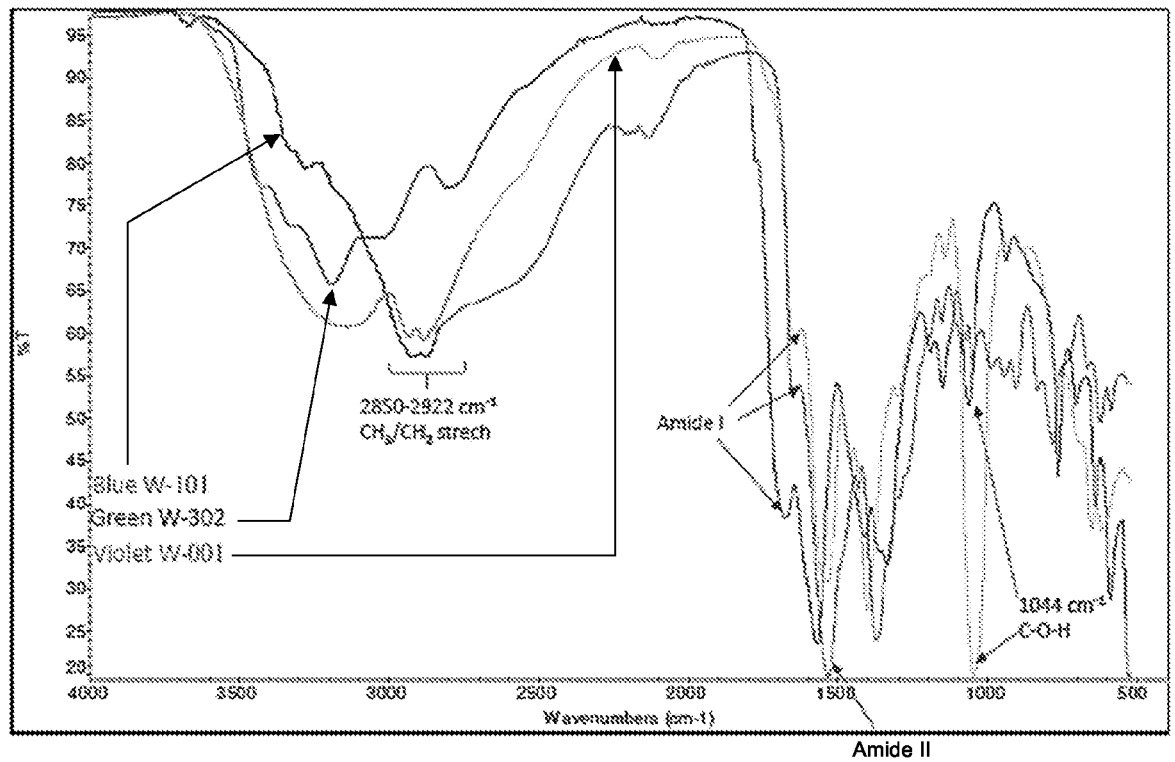

FIGS. 12 and 13 illustrate that synthesizing PCN's using the same starting material, can lead to different emission characteristics that can be used in the compositions and methods provided. For example starting with Urea and Citric Acid, reaction with urea, yielded PCN that is soluble in water and having peak emission wavelength at ~522 nm (See e.g., FIG. 3C), similarly, PCNs formed using CA and EDA with water as solvent, yielded blue-emitting compounds with peak emission wavelength at 445 nm (See e.g., FIG. 1C), while TRIS and CA produced PCN having emission peak wavelength at 410 nm. As illustrated in FIG. 12, the composition differences can generate PCN's of different emission characteristic, that are composition rather than size-dependent. FT-IR comparison is provided in FIG. 13.

TABLE I

Elemental Analysis for various PCNs.

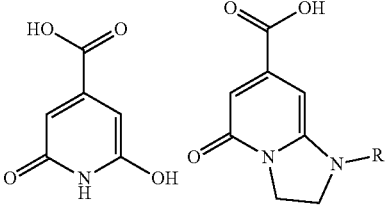

| Element Conc. | PCN | | |
|---|---|---|---|
| N | 30.59 | 22.5 | 7.49 |
| C | 32.02 | 41.9 | 42.4 |
| H | 3.65 | 8.09 | 7.9 |
| O | 31.25 | 18.51 | 42.21 |

Being in a suspended system, the PCN's can be suspended in a continuous phase that has only limited solubility in a non-polar bulk liquid and be incorporated or admixed into the non-polar bulk liquid such that the concentration of the continuous phase of the PCN's suspended system (as differentiated from the continuous phase of some of the non-polar bulk liquids sought to be tagged and/or identified, and/or authenticated, for example in petrol), is lower than the solubility limit at the anticipated relevant reference temperature. The term "solubility limit" refers to the point at which no additional amount of a constituent, (e.g. water in non-polar liquid, or oil) is miscible or dissolvable with the bulk liquid, as measured at 20° C. and 101 kPa (1 Atm.). Unless otherwise stated, all solubility related parameters are determined at 20° C. and 101 kPa referred to as STP.

In an embodiment, the term "non-polar liquid" refers either to a bulk liquid without significant partial charges on any atoms (e.g. hydrocarbons) or to a bulk liquid in which the polar bonds are arranged in such a way that the effects of their partial charges are cancelled out (e.g. chloroform) and to liquids that have a dielectric constant of less than about 5 (e.g., hexane and various hydrocarbon-based oils). Conversely, the term "Polar liquids" or "polar bulk liquids" refers in an embodiment to a bulk liquid which has a significant polarity due to the presence in its molecular structure of atoms other than carbon and hydrogen.

The PCN's can be unmodified or modified to maximize thermodynamic compatibility with the PCN's suspended system's continuous phase, or in other words the interfacial free energy of the PCN's is configured (by either employing surface modification or not), to be lower in the PCN suspended system's continuous phase, than in the non-polar bulk liquid, than the non-polar bulk liquid's continuous phase, thereby promoting partitioning the PCN's to the suspended system's continuous phase.

Furthermore, the PCN suspended system's continuous phase can be configured to match the viscosity of the bulk liquid, or when the bulk liquid itself is a suspended system, the bulk liquid continuous phase. It is understood that for mitigating toxicity, the PCN's cannot be magnetized or otherwise be semiconducting PCNs. As used herein, the term "continuous phase" means dispersion medium, namely the liquid in the disperse system in which the PCN's are suspended, with or without the presence of additives.

Accordingly and in an embodiment, provided herein is a method of tagging a liquid, comprising: providing a composition comprising PCNs suspended in a continuous phase having at least one of: a limited solubility in the tagged liquid and substantially low concentration of PCNs; and incorporating the suspension into the liquid, wherein the suspension is incorporated at a concentration of continuous phase that is at least one of being below the solubility limit of the suspension's continuous phase in the bulk liquid and a concentration that cannot be observed unaided to the naked eye. The term "naked eye" as used herein refers to human visual perception that is unaided by enhancing equipment.

The PCNs used in the systems, compositions and methods for selectively and specifically tagging, and/or identifying, and/or authenticating bulk liquids as described herein can be, for example: carbon nanotube quantum dots, graphene quantum dots, graphene oxide quantum dots or a combination of PCNs comprising one or more of the foregoing. The carbon nanotube quantum dots can be single wall nanotube (SWNT), or multi-wall nanotube (MWNT), or their combination. As indicated sought to be tagged and/or identified, and/or authenticated, the PCN's can be unmodified, making them more thermodynamically compatible with aqueous continuous phase and therefore appropriate for tagging hydrophobic bulk liquids, for example crude oil.

For example, the PCN's is an unmodified graphene quantum dot (GQD) suspended in water and the bulk liquid sought to be tagged and/or identified, and/or authenticated is crude oil. The PCN suspension can be admixed into the crude oil either in flow, for example using a dosing pump and a static mixer following the dosing point in the pipe, such that the concentration of the water in the oil does not exceed the solubility limit of water in crude oil at room temperature (about 23° Centigrade), about 30 ppm (Volume PCNs continuous phase/Volume crude oil). Alternatively, the PCN's suspension can be admixed into a container of the crude oil (e.g., a tanker, a well, or an in ground/above ground tank), and stirred.

The solubility limit when the bulk liquid is non-polar, can be tailored to the liquid sought to be tagged and may increase or decrease. Water solubility in various oils is related to the ratios of paraffin, naphthenic, and aromatic compounds, with the solubility limit at 20° C. varying between about 30 parts per million (ppm) to about 200 ppm for example, between about 40 ppm and about 80 ppm. Notwithstanding, to achieve even greater economic advantage, concentration of PCN's in the bulk liquid can be adapted to be; for example between about 0.1 ppb (parts per billion) to about 100 ppb.

In another example, the PCN can be used in concentration of between 8 ppb and 999 ppm and have a plurality of PCN with discrete peak emission spectra, such that the concentration used is not visible to the naked eye, nor are the plurality of peak emission spectra resulting from the PCN composition used, is discernable using full wavelength (e.g., 190-720 nm) EMR source.

In both polar and non-polar bulk liquids, the incorporation of the PCN's suspended system is adapted to inhibit separation, whether by sedimentation or by creaming. This can be done by controlling the pressure and orifice diameter of the dosing point in the pump if admixing takes place during flow, as well as the relative flowrate of the bulk liquid in the pipe, or the admixing rate and use of atomizing nozzles if admixed to a bulk container while controlling the stirring rate (when available). Other parameters that can be used to control the separation rate can be storage or flow temperature and the viscosity of the PCN's suspended system continuous phase. Accordingly, and in an embodiment, the composition comprising the modified or unmodified PCN's further comprise viscosity modifiers, for example polymers (e.g., xanthan gum and the like) and/or other colloidal particles.

Figure 1B:
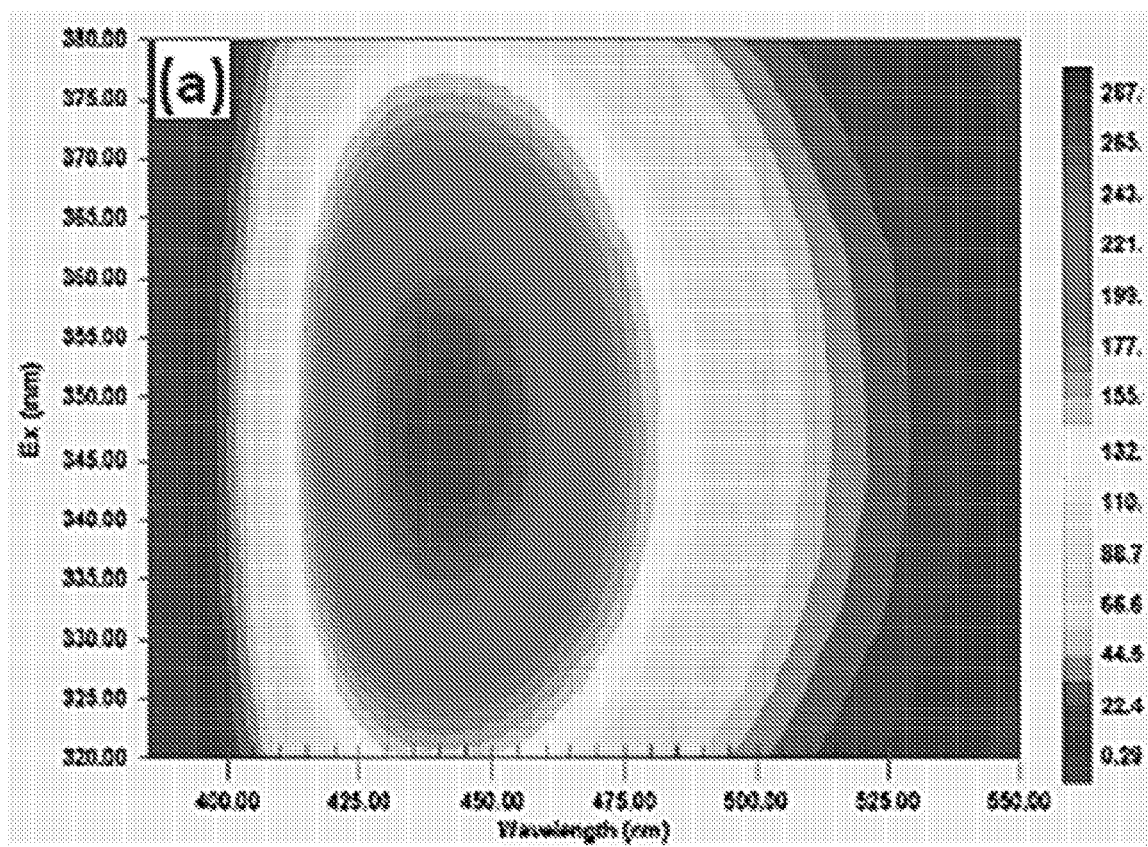
Figure 1C:
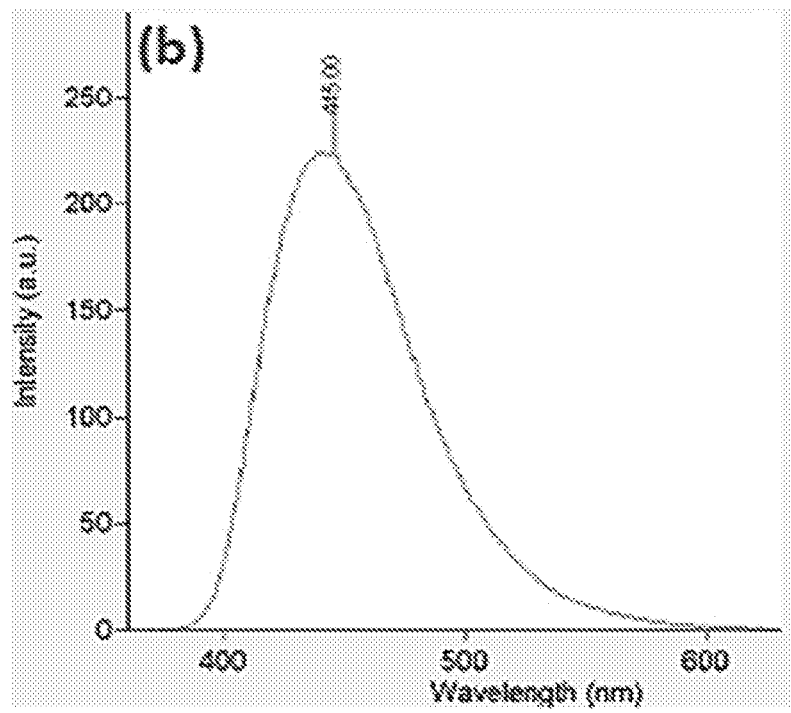
Figure 1D:
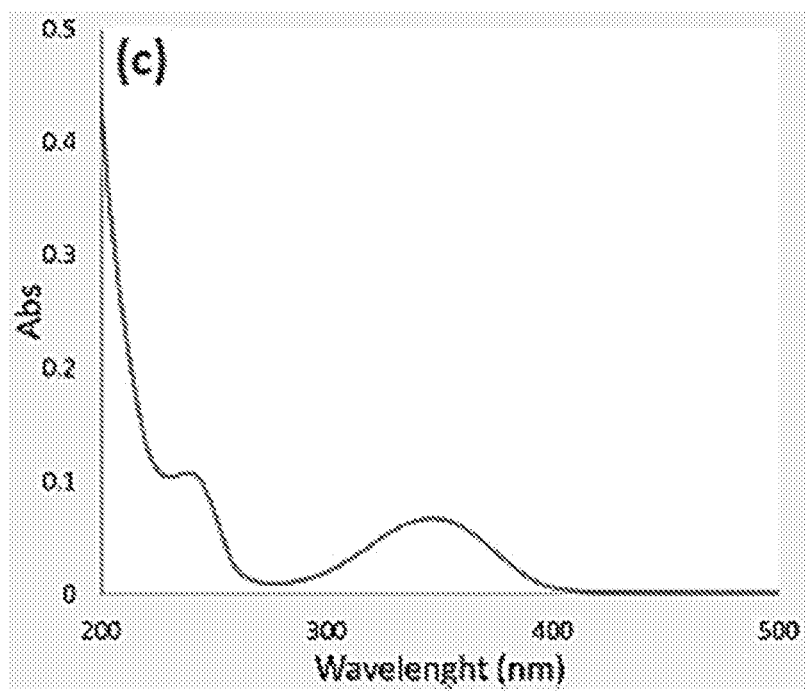
Figure 2A:
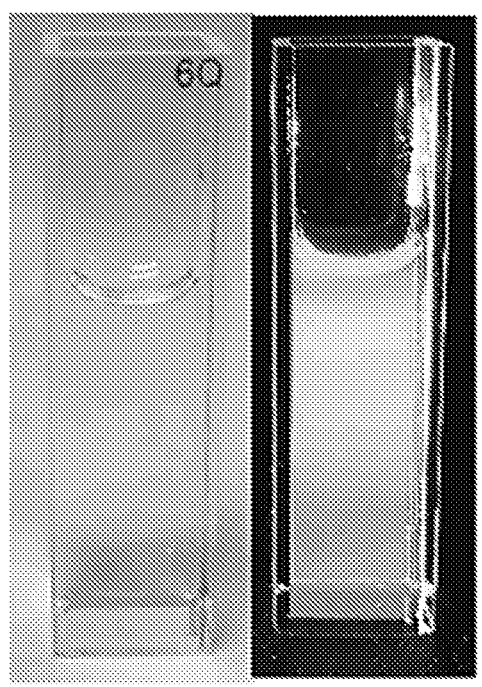
FIG. 2A, shows the luminescence characteristic of PCNs having a size emitting cyan luminescence, with excitation and emission contour map illustrated in FIG. 2B, photoluminescence emission spectra at 420 nm excitation in FIG. 2C, and absorption spectra illustrated in FIG. 2D.
Figure 2B:
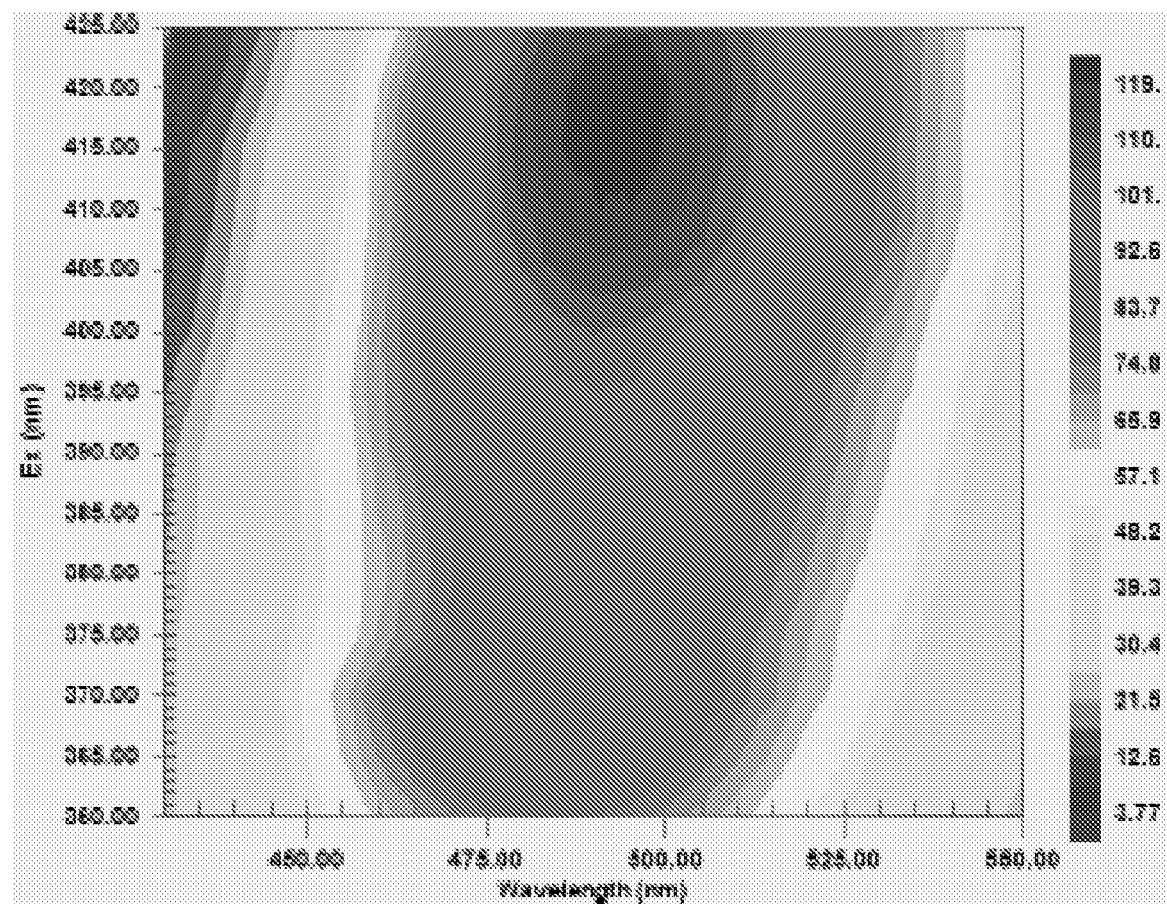
Figure 2C:
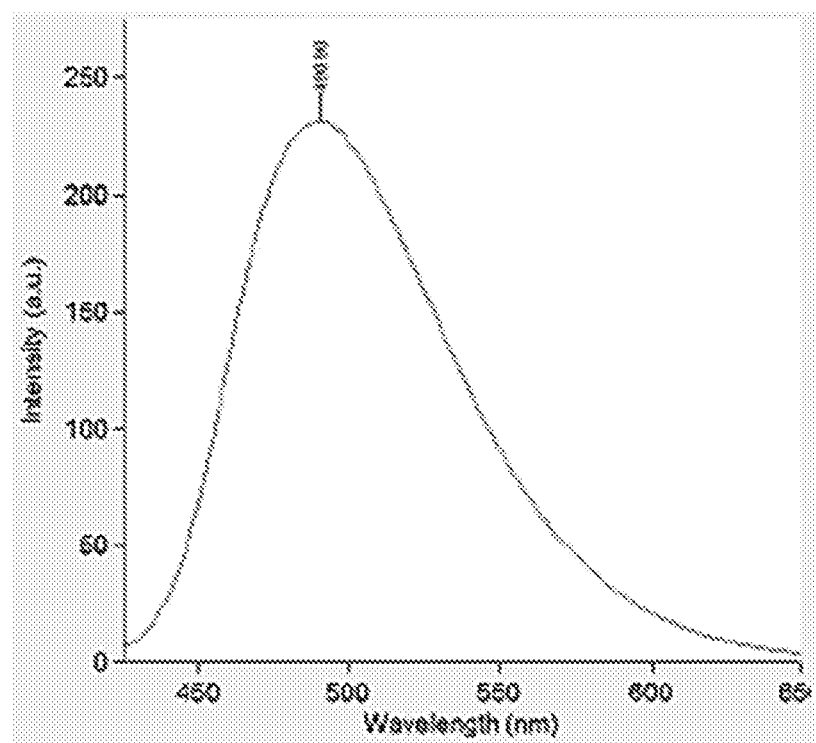
Figure 2D:
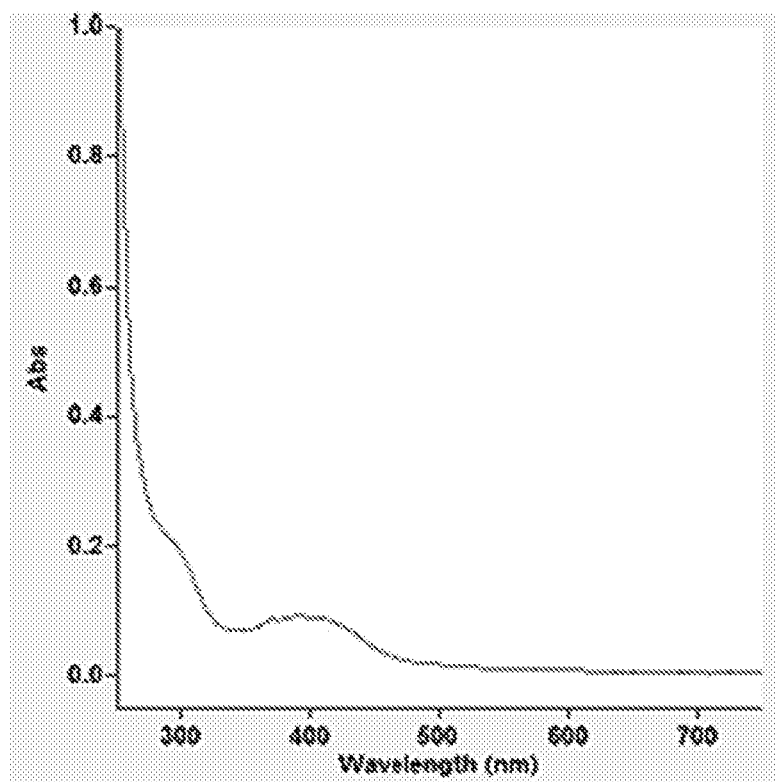
Figure 3B:
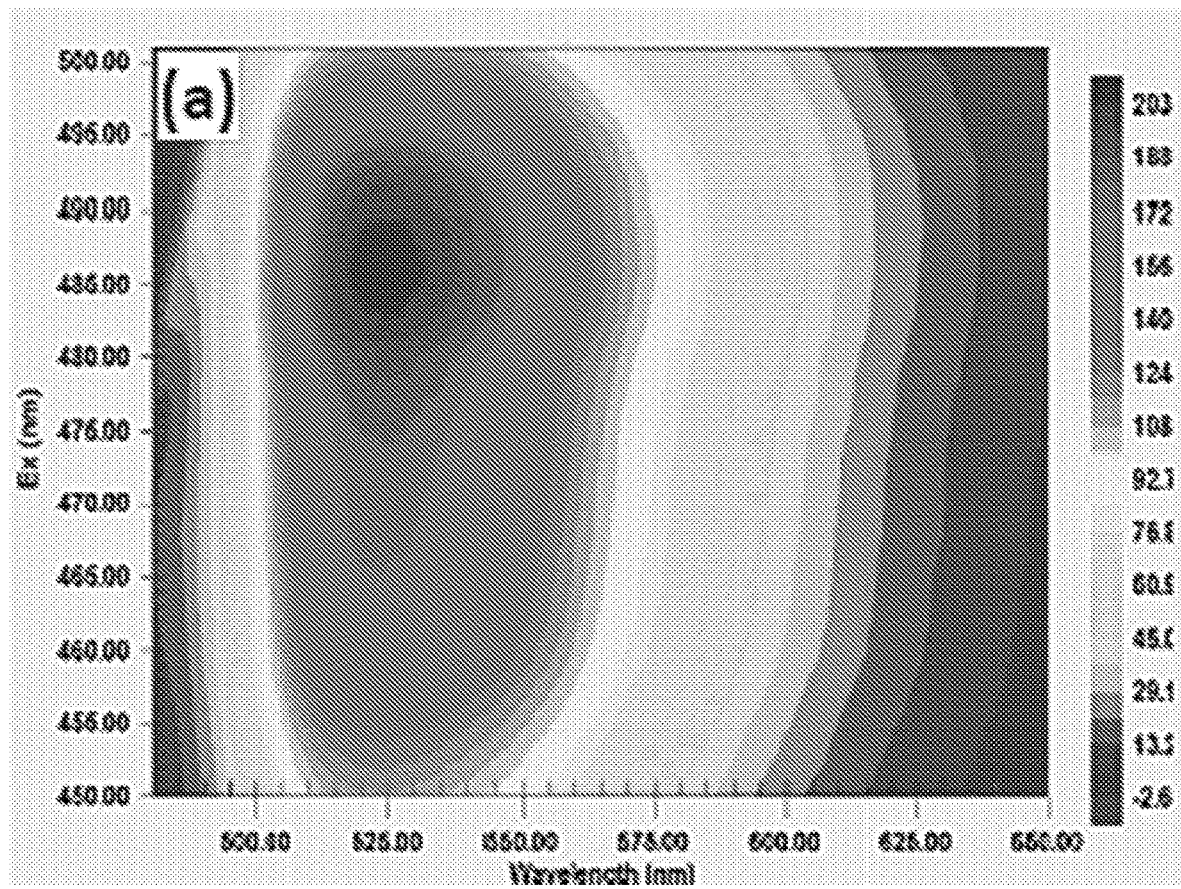
Figure 3C:
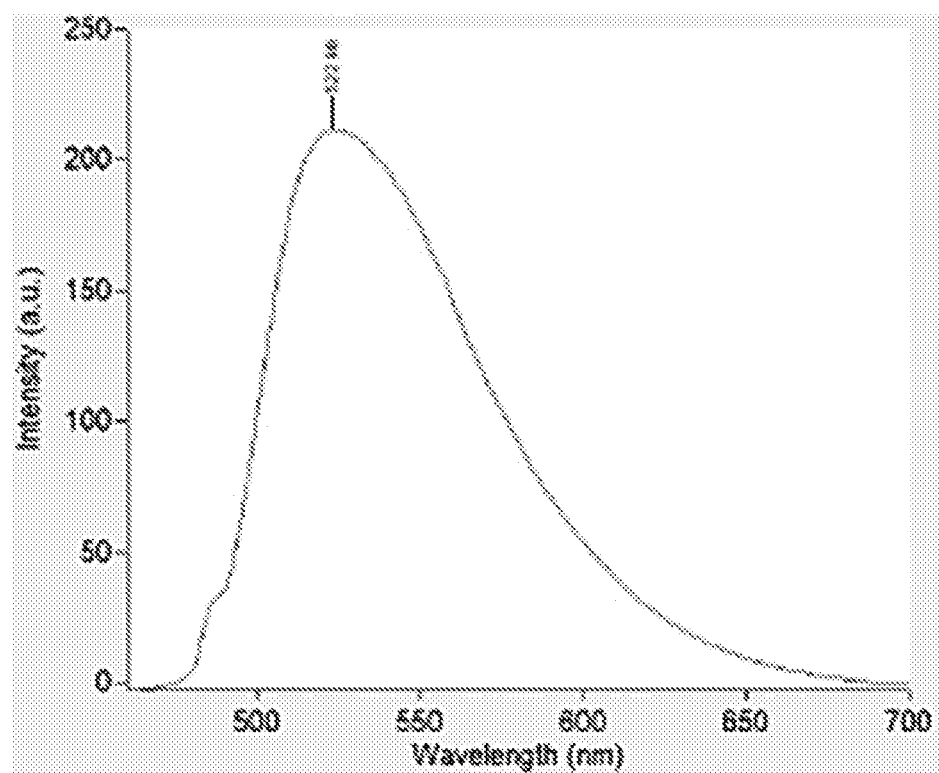
Figure 3D:
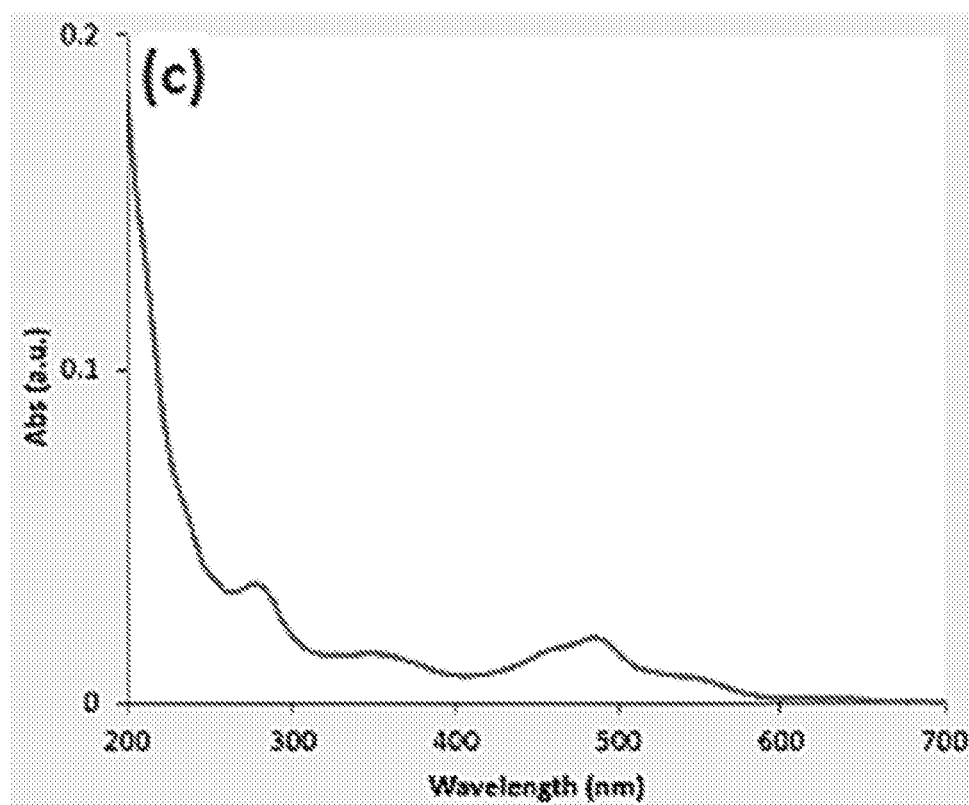

Furthermore, the PCN's can be of a predefined single size, in other words having a substantially selected, predefined and known monomodal particle size distribution. As illustrated in the figures, the PCN's can have a single size, for example having area average particle size ($D_{2,1}$) of less than 5 nm, providing blue luminescence (See e.g., FIG. 1A) when excited at 350 nm, yielding maximum emission at 445 nm (see e.g., FIG. 1C); or a area average particle size ($D_{2,1}$) of less than 4 nm, providing cyan luminescence (See e.g., FIG. 2A) when excited at 420 nm, yielding maximum emission at 490 nm (see e.g., FIG. 2C), or an area average particle size ($D_{2,1}$) of less than 3 nm, providing aqua-green luminescence (See e.g., FIG. 3A) when excited at 485 nm, yielding maximum emission at 525 nm (see e.g., FIG. 3C). Alternatively, the composition of suspended PCN's can be a mixture of predefined, selected and known PCN sizes, which, depend on the sizes and/or composition (type) and/or continuous phase characteristics (e.g., toluene or hexane) and/or relative concentration of PCN, emission spectra profile (see e.g., FIG. 3C), the excitation/emission contour map (see e.g., FIGS. 1B, 2B, and 3B), and the absorption spectra profile (see e.g., FIGS. 1D, 2D, and 3D), or their combination, would represent a unique profile of the PCN mixture when excited at least one of a predetermined wavelength, a wavelength range that is smaller than the full visible light spectrum (in other words at an electromagnetic wavelength range that is no more than 300 nm between 320 nm and 920 nm, and a plurality of wavelength ranges, each which is smaller than the full visible light spectrum (in other words at an electromagnetic wavelength range that is no more than 300 nm between 320 nm and 920 nm. The excitation need not be at a continuous range but can be at discrete wavelengths or wavelength ranges while the excitation occurs simultaneously or sequentially. As illustrated in FIGS. 1B, 2B, and 3B, all the PCN's exhibit positive Stokes shift and are thus Stokes markers. In an embodiment therefore, the PCN's used in the disclosed systems, compositions and methods disclosed and claimed herein, are not Anti-Stokes markers.

The composition and methods for tagging a bulk liquid can be used in the methods of identifying the tagged liquids, and are implementable in the systems disclosed herein. Therefore, in another embodiment, provided herein is a method of identifying a tagged non-polar liquid, implementable in a tagged non-polar liquid wherein the non-polar liquid was tagged by incorporating a composition comprising PCN's suspended in a continuous phase having limited solubility in the tagged non-polar liquid at a concentration of continuous phase of the PCN suspension that is below the solubility limit of the continuous phase of the PCN suspension in the bulk non-polar bulk liquid, the method comprising: obtaining a sample of predetermined volume from the bulk non-polar liquid; admixing into the bulk non-polar liquid the continuous phase of the PCN suspension to a concentration above the solubility limit of the continuous phase in the tagged non-polar bulk liquid; partitioning the PCN suspension's continuous phase from the tagged non-polar bulk liquid; exposing the partitioned continuous phase to electromagnetic radiation (EMR) source at at least one of a predetermined wavelength, a predetermined wavelength range and a plurality of predetermined wavelength ranges; and detecting: excitation/emission contour map, and/or emission spectra, and/or absorption spectra of the partitioned continuous phase.

Using predetermined protocols or procedures, "detecting", which in another embodiment also includes quantifying excitation/emission contour map, and/or emission spectra, and/or absorption spectra of the continuous phase can be done, by measuring luminescence of the measured sample. Luminescence spectroscopy involves the measurement of photon emission from molecules. It can include photoluminescence such as fluorescence and phosphorescence, which are emissions from a substance resulting from its excitation by radiation absorption, and chemiluminescence, where the emission is induced by a chemical reaction. The emitted radiation is characteristic of the molecular structure and composition.

In an embodiment, "detecting" refers to the quantification of the amount or of carbon dots present in a sample, i.e. measuring the amount or concentration of the quantum dots semi-quantitatively or quantitatively. The detection of the amount of the quantum dots can be accomplished in a variety of ways known to the skilled person or detailed herein. In accordance with the present disclosure, detecting the amount of the quantum dots can be achieved by all known means for detecting the amount of the quantum dots in a sample, provided that they are adapted to specifically detect the quantum dots of the present disclosure and are compatible with its requirements. The term "amount" as used herein encompasses the absolute amount of the quantum dots referred to herein, the relative amount or concentration of the quantum dots referred to herein as well as any value or parameter which correlates thereto. Such values or parameters comprise intensity signal values from all specific physical or chemical properties obtained from the quantum dots referred to herein by measurements. It is to be understood that values correlating to the aforementioned amounts or parameters can also be obtained by all standard mathematical operations and protocols or procedures specified herein.

For example, by using a photodetector array (e.g., a PIN diode array) with different color filters based on the PCN's used in the suspended system, whether of a single size or a mixture of several sizes PCN's, as well as provide an UV/VIS/NIR bandpass(es) color filter(s) operably coupled to a photodetector array. Alternatively, a diffraction grating coupled to a photodetector array can be used to determine the spectrum profile emitted from the PCN's. Detection can be quantified, yielding peak emission, full width at half maximum (FWHM), intensity and area under the curve (AUC), as well as ratios of the foregoing, as a function of excitation wavelength; all which can be added to the linked library database at the source and used to compare with the test sample obtained by an end user or intermediate downstream (pipeline or supply chain).

Other methods can be used in other embodiments to provide the necessary quantitative measurements for detecting and authenticating the PCN's described. For example, Infrared (IR) spectroscopy is based on the interaction with chemical substances of infrared irradiation having a wavelength between 0.77 µm and 1000 µm. A segment of IR spectroscopy, referred to as near infrared (NIR) spectroscopies, uses radiation wavelengths between about 0.77 µm and about 2.5 µm. IR and NIR spectroscopies generally involves the absorption of radiation as it passes through a sample. The absorption frequencies can therefore provide information regarding the chemical and physical characteristics or the molecular structure of the irradiated substance and its composition. Likewise, Ultraviolet (UV) and visible (VIS) spectroscopic methods employ UV radiation having wavelengths between about 200 nm and about 350 nm and visible radiation with wavelengths between about 350 nm and about 770 nm. UV/VIS techniques can be used in an embodiment, to measure the absorption of the exposing radiation by molecular electronic transitions; the particular wavelengths absorbed are characteristic of the molecular structure of the substance under investigation. In addition, Raman spectroscopy can be used to obtain chemical, physical, and molecular information of the samples sought to be identified and/or authenticated. In it incident radiation interacting with the PCN's can undergo scattering, which occurs in all directions; the radiation may be scattered elastically or inelastically. The inelastically scattered radiation is referred to as Raman scatter. The wavelengths and intensities of this radiation comprise a Raman spectrum that provides chemical and structural information regarding the irradiated material. Accordingly and in another embodiment, the Raman Spectrum fingerprint is used as an authenticating information for the sample. Specific procedures or protocols for the detection can be used as an authentication step in the methods described and claimed.

Figure 4:
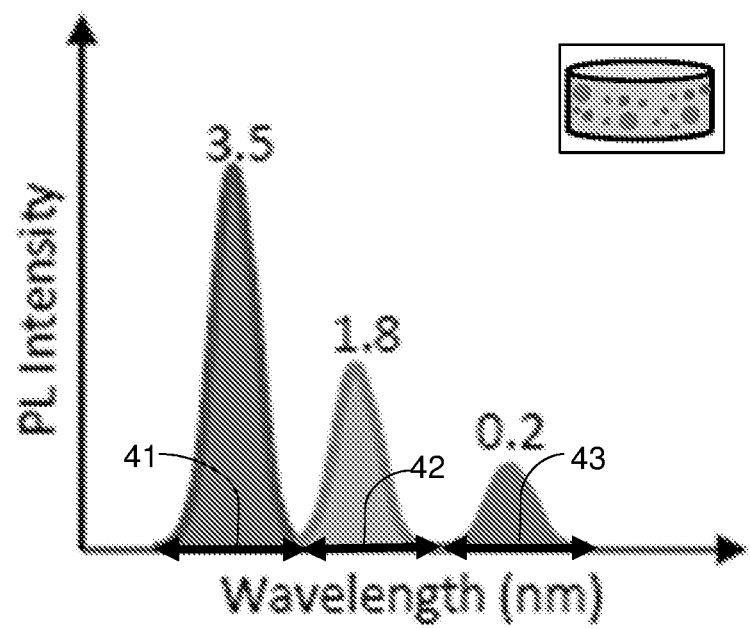
FIG. 4, illustrates a schematic of luminescence emission of a mixture of PCNs.
Figure 5A:
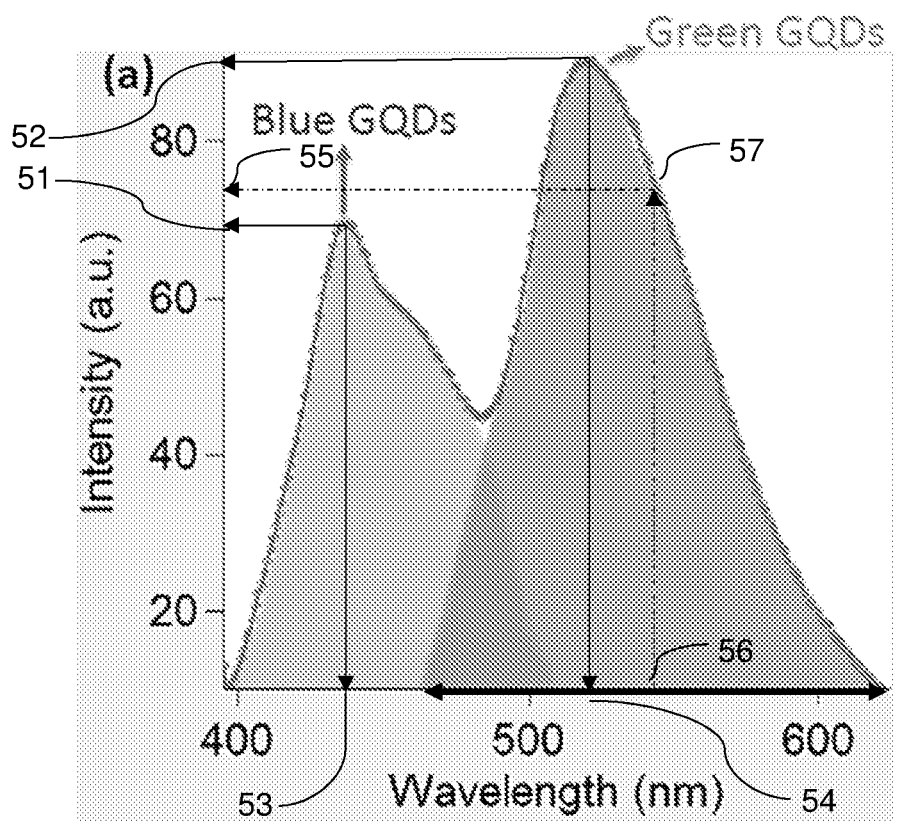
FIG. 5A, illustrates the emission spectra of a PCN mixture with excess blue PCN, with excess green PCN illustrated in FIG. 5B.
Figure 5B:
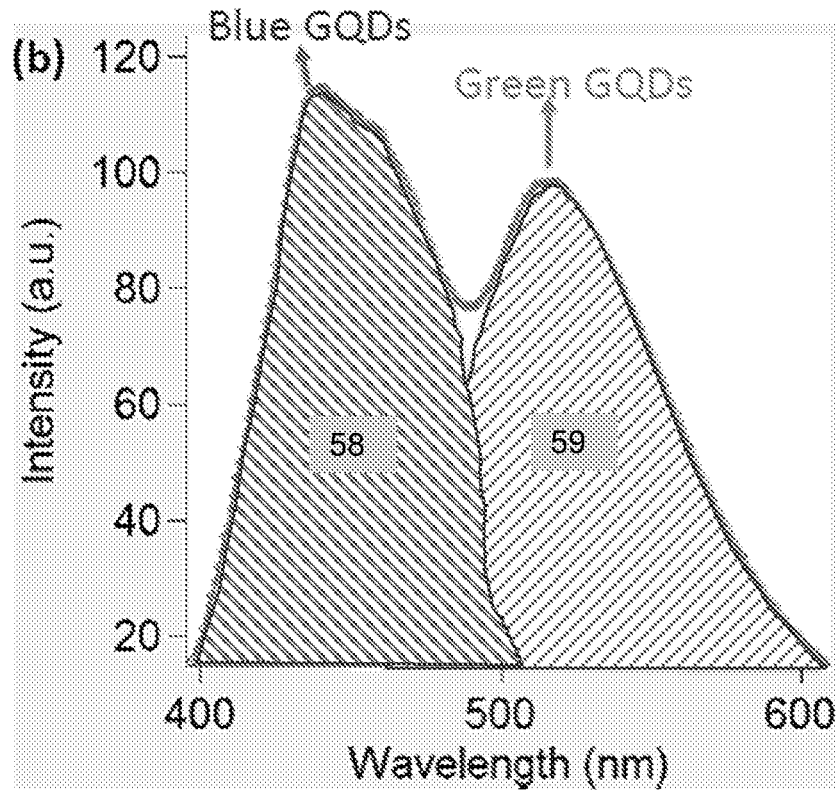
Figure 9A:
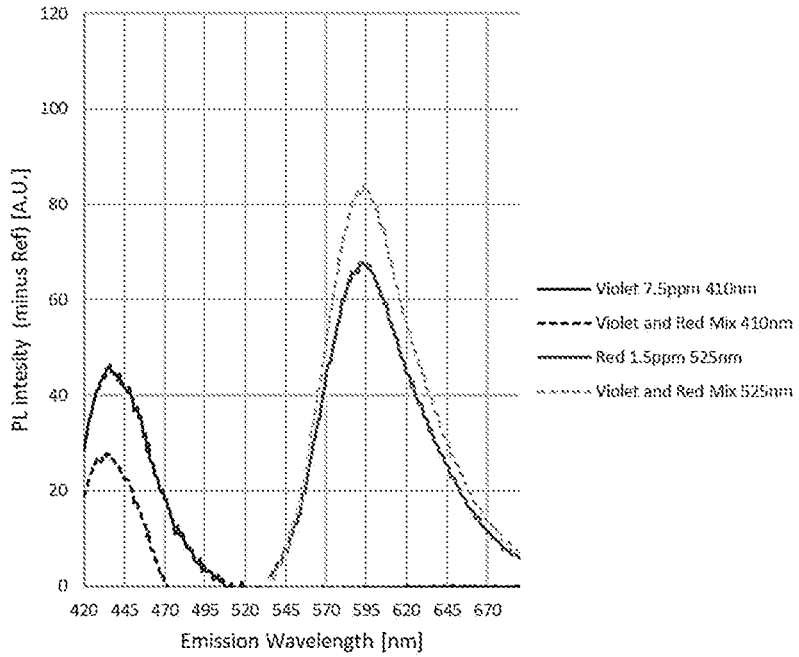
FIG. 9A, shows emission spectra of mixed violet and red PCNs in a synthetic engine oil (Syntrax 75W 140), with mixed blue and red PCNs emission in the same oil, illustrated in FIG. 9B.

An embodiment of the emission spectra of a mixture of PCN's of varying sizes is illustrated in FIG. 4 (see e.g., FIG. 4 inset), with FIGS. 5A and 5B, illustrating an example of green and blue PCNs. As a point of clarification, the control over peak emission spectra is not necessarily solely a function of size, but of other factors as well, for example; the extent and location of surface defects in the PCN, type and degree of substitution of various functional groups (e.g., carboxylate) as well as uniformity of size distribution and others. In addition, the same PCN composition may nevertheless exhibit different peak emission wavelength, depending on the solvent used as the delivery vehicle for the PCN. An example is illustrated in Table I and FIGS. 9A, 9B and 13-15. As illustrated TPN and hydrazine were used and as shown in FIG. 9A, excitation at 410 nm caused peak emission at 445 nm when the solvent is toluene, whereas in FIG. 9B, the same material (TPN+hydrazine) in the same (synthetic motor) oil, using hexane as the carrier, shows peak emission at 435 nm. FIGS. 13 and 14 illustrate the FT-IR composition data of the blue and violet emitting PCNs respectively, with their comparison shown in FIG. 15.

Accordingly, it is contemplated that PCN's having exactly the same overall average $D_{2,1}$ particle size (e.g., 5.0 nm), would nevertheless have peak emission spectra that is shifted between about 20 nm and about 80 nm.

Turning to FIG. 5A, showing the emission spectra of a mixture of blue and green emitting PCNs at known fractional concentration. The mixture can yield various ratios that depend on the type and concentration of PCNs used. The mixture's unique composition can then provide an array of parameters that can then be used to identify and authenticate the bulk liquid tagged with that mixture. The parameters can be, for example, the peak emission intensity ratio (e.g., 51/52), wavelength ratio at half the (calculated) baseline of each PCN species (see e.g., FIG. 4, R=43/42, 43/41, 42/41, or FIG. 5A, 56), and/or the intensity at half the baseline (see e.g., FIG. 5A, 55). In addition, ratios of area under the curve can be used as a parameter (see e.g., FIG. 5B, 58/59). It is contemplated that not just the scalar ratios are used, but also any transformation thereof can also be considered, for example, a reciprocal of the ratio (1/R), –log R, ln R etc. Furthermore, many bulk liquid used commercially are further tinted with a dye that can yield substantial luminescent background. That background can be subtracted from the observed emission spectra, yielding a "cleaner" emission spectra that substantially eliminate the impact of the dye incorporated to the bulk liquid. Accordingly and in an embodiment, if the tagged liquid is tinted with dye, further comprising a step of correcting the baseline by subtracting background emission corresponding to the dye.

The term "tinted" refers to a tagged liquid containing a coloring agent addition, and having an absorption spectrum for visible radiation that varies in response to at least actinic radiation. Thus for example, in one non-limiting embodiment, the tagged liquid can have a first color characteristic of the coloring agent and a second color characteristic of the combination of the coloring agent and the tagged liquid when exposed to actinic radiation. In yet another embodiment, baseline correction can be configured to substantially remove the effects of the tinted tagged liquid on the emission spectra measured, leading to a clearer emission spectra.

The term baseline correction refers to the procedure of relativizing the emission spectra signal of interest with respect to a control (baseline) signal (e.g., the bulk liquid without the tinting dye). There are various methodologies for baseline correction (or subtraction). For example, smoothing, which first identifies the baseline points following differentiation with a wavelet transform. The baseline points are then fit using "Smoother" algorithm. Two parameters are available for controlling this algorithm. The first parameter effects the size of regions that are used in identifying the baseline regions, while the second parameter controls how closely the fitted baseline function matches the points identified as baseline. These two parameters can be stored in the authentication database as part of the authentication protocol. Another method that can be used, is a polynomial method, which first identifies the baseline regions by comparing the maximum intensity in a series of window regions to the estimated noise level of the spectrum. The baseline regions are then fit using a polynomial equation of specified order (n). Two parameters can be used (and stored) for controlling this algorithm. The first parameter effects the size of regions that are used in identifying the baseline regions (e.g., wavelength range), while parameter (n) controls the order of the fitted polynomial and most typically be between 2 and 16 (depending on the number of discrete PCNs each having a discrete peak emission spectra wavelength used in a given mixture.

Figure 9B:
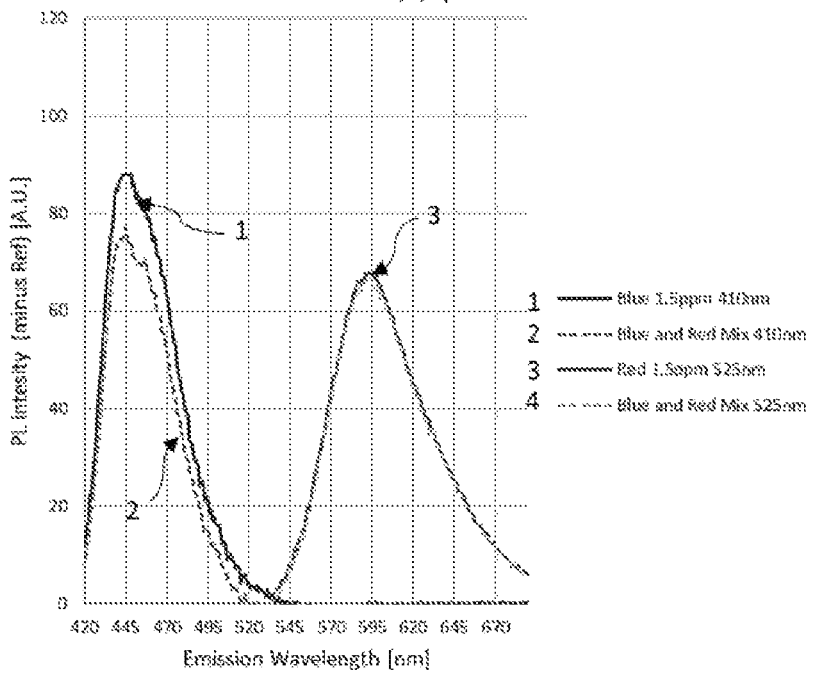

Other baseline correction methods can also be implemented, for example, a sine method where baseline region is identified by comparing the maximum intensity in a series of window regions (e.g., emission wavelength ranges), to the estimated noise level of the spectrum. The baseline regions are then fit using an equation formed from the sum of a specified number of sine and cosine functions. Two parameters become available for controlling this algorithm, which can be used in the authentication methods described herein. The first parameter effects the size of wavelength range that is used in identifying the baseline for example, between 420 nm and 695 nm. The second parameter controls the number of sine and cosine functions. For example A value of n=2 would specify the use of $\sin(2\cdot\pi\cdot f)+\cos(2\cdot\pi\cdot f)$, while a value of 4 would specify the additional use of $\sin(4\cdot\pi\cdot f)+\cos(4\cdot\pi\cdot f)$, and so on to $\sin(n\cdot\pi\cdot f)+\cos(n\cdot\pi\cdot f)$, etc. These values again can be specified as part of the authentication protocol. Additionally or alternatively, baseline correction can be affected by, for example, simply subtracting the average of the values in a predetermined spectrum edge points from each data point. For example, as illustrated in FIG. 9B, the average values in arbitrary intensity units (a.u.) at the 400 nm and at 600 nm. Fraction of the spectrum used to normalize the baseline is typically the fraction of the left-hand and right-hand spectral window used to define baseline, which is greater than zero and less than ⅓ of the full spectrum window. Here too, the spectrum edges used for the baseline correction can be incorporated into the methods of authentication described and claimed.

Other appropriate methods can also be used and parameters controlling the correction be incorporated to the authentication method.

Figure 6:
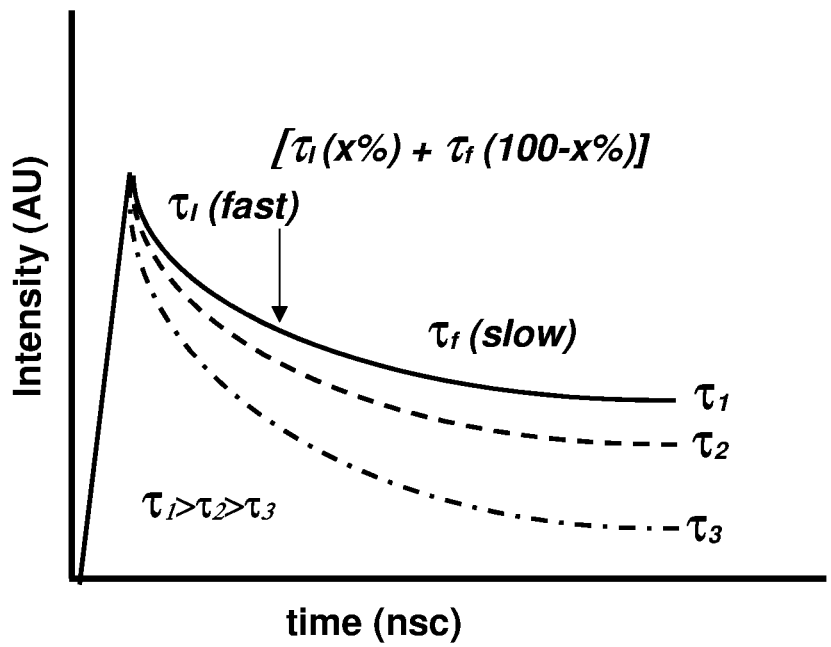
FIG. 6, is a schematic illustrating the typical decay behavior of various PCNs both pure and in mixtures.

As illustrated in FIG. 6, authentication parameters can be for example, the characteristic decay time for the sample in nanoseconds. It was observed, that while typical characteristic decay times (in water) for PCN's is between about 0.7 ns and about 10 ns, for example, between about 1.2 and about 7 ns, or between about 2.0 ns and about 5.0 ns. The characteristic decay time will depend on size and composition, as well as the functional groups substituted on the PCN's used. Moreover and as illustrated in FIG. 6, decay curves may exhibit more than a single characteristic decay time ($\pi_D$). Accordingly and in an embodiment, the detector, which can be a photoluminescence detector, can be configured to measure photoluminescence decay at a predetermined wavelength and liquid medium (continuous phase);

and further compute the characteristic decay time and/or times for the examined sample. The characteristic decay time and/or times can and are used in an embodiment as a parameter based on which the sample can be identified and/or authenticated. As an addition layer of authentication; in samples exhibiting more than a single characteristic decay time and/or times, the fraction of the curve associated with each characteristic decay time can and is used as an identification and/or authentication parameter.

The electromagnetic radiation source can be a light emitting diode (LED) adapted to provide light at a discrete wavelength, a LASER source (e.g., a laser diode or diodes providing a predetermined wavelength), or a light source coupled to appropriate optical filter. As indicated, there can be more than one LED thus providing simultaneous excitation at various wavelengths, as there can be more than a single LASER source or light source with optical filters that limit the wavelength spectrum exciting the PCN's. In an embodiment, a single EMR source, at a single wavelength can be used to excite all PCNs is used, regardless of size. Although under these circumstances there may be an Anti-Stokes behavior exhibited, the intensity of the peak emission will be lower than that of had the excitation been below the peak emission and therefore the PCN's are still not considered Anti-Stokes markers.

One, all, or some of these electromagnetic radiation sources can be incorporated in a handheld housing having: a display; an orifice configured to receive a transparent vial (e.g., a cuvette); a processing module comprising a processor in communication with a linked library containing original emission spectra at a specific wavelength, excitation and emission contour map, absorption spectra, or their combination of the tagging PCNs incorporated in the liquid sought to be selectively and specifically identified and/or authenticated; the processor further being in communication with: the electromagnetic radiation source; a detector (e.g., a photodetector) configured to detect fluorescence, phosphorescence, chemiluminescence or their combination (and can further comprise additional optical color filters); the display; and a non-volatile memory having thereon a processor-readable medium with a set of executable instructions configured to: receive a reading from the detector; retrieve from the linked library at least one of: a predetermined excitation and emission contour map, and absorption spectra; and if the emission spectra at a specific wavelength, excitation and emission contour map, absorption spectra, or their combination, retrieved from the detector correlates with the excitation/emission contour map, and/or emission spectra, and/or absorption spectra at the predetermined specific wavelength, wavelength range or plurality of wavelength ranges' segments that were retrieved from the linked library, authenticating the tagged liquid using the display; else identifying the liquid as non-authentic.

Figure 7:
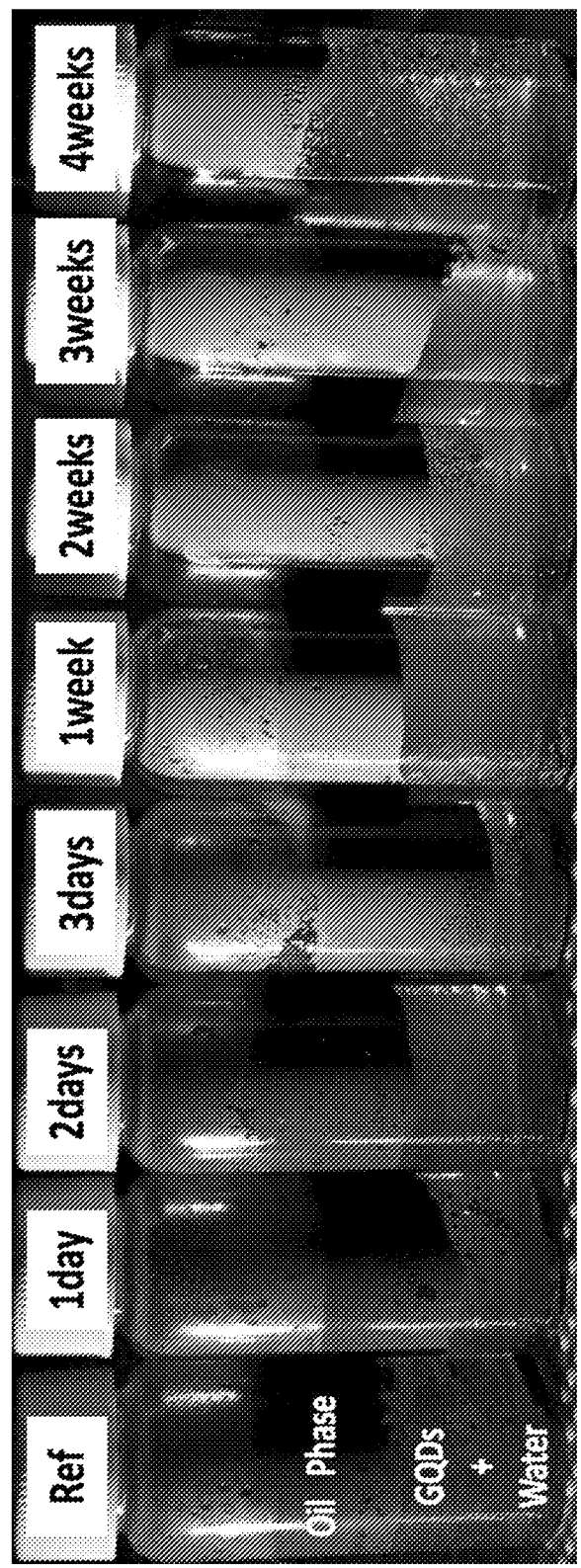
FIG. 7, shows partition of PCN in oil to the aqueous phase over time.

The step of partitioning the PCN's suspended system's continuous phase, now above its solubility limit in the non-polar bulk liquid, can be by inducing phase separation between the non-polar bulk liquid and the PCN's suspended system's continuous phase, for example, by shaking, heating, adding detergent or other surfactants, filtering and the like steps, configured (based on both the non-polar bulk liquid's properties and the PCN's suspended system's continuous phase properties) to accelerate phase separation. The step of partitioning can further include a step of separating the partitioned PCN's suspended system's continuous phase, for example by removing the sediment from the sample vial (see e.g. FIG. 7) and can further include a step of concentrating the PCN's suspended system's continuous phase. Not wishing to be bound by theory, since the interfacial energy of the PCN's is lower in the continuous phase, it is reasonable to expect that the PCN's will remain or migrate from the non-polar bulk liquid to the partitioned PCN's suspended system's continuous phase and thereby provide a true representation of the PCN's in the non-polar bulk fluid.

In addition, partitioning can be by adsorption onto solid media, such as silica beads and the like.

As used herein, the term "phase separation" refers to the separation of a multi-phasic composition of matter, in other words, to a composition having various components that are different in terms of physico-chemical homogeneity, to two (or more) compositions that are more homogeneous in terms of their physico-chemical characteristics.

Additionally or alternatively, provided herein is a method of identifying a tagged liquid, implementable in a tagged liquid wherein the liquid was tagged by incorporating a composition comprising PCNs at a concentration of between 8 ppb and 999 ppm, wherein the PCNs have at least two discrete peak emission wavelength, the method comprising: obtaining a sample of predetermined volume from the bulk liquid; detecting the fluorescent emission spectra of the bulk liquid with the PCNs; and subtracting the fluorescent emission spectra of the bulk liquid without the PCNs or "blank" sample.

The methods using the tagged liquids disclosed and claimed herein, implemented using the compositions and systems described herein can further comprise comparing the detected emission spectra to a predetermined emission spectra corresponding to an authentic identity of the bulk liquid; and if the emission spectra correlates with the predetermined emission spectra, authenticating the tagged liquid; else identifying the liquid as non-authentic. The term "authentic" as used herein means that the excitation/emission contour map, and/or emission spectra, and/or absorption spectra of the partitioned continuous phase of the PCN suspended system has high correlation with the excitation/emission contour map, and/or emission spectra, and/or absorption spectra of the tagged bulk liquid obtained at the original source and initial point of the bulk liquid tagging.

To clarify, in the description that follows, embodiments are described with reference to acts that are performed by one or more computing systems. These computing systems can be co-located or remote from each other and connected through various types of networks. The computing systems can be, for example, the handheld device disclosed, a backend management server with the bulk liquid database library, and the like. If the computing systems are distributed (in other words not co-located or otherwise hardwired), the housing comprising the EMR source can further comprise a transceiver configured to initiate communication with remote computing systems.

If such acts are implemented in software, one or more processors of the associated computing system(s) that performs the act direct the operation of the computing system in response to having executed computer-executable instructions. An example of such an operation involves the manipulation of data. The computer-executable instructions (and the manipulated data) may be stored in the memory of the computing system. Computing system may also contain communication channels that allow the computing system to communicate with other processors and sensors over, for example, service bus.

Embodiments described herein may comprise or utilize a special purpose or general-purpose computer including computer hardware, such as, for example, one or more processors (e.g., central processing module, CPM) and system memory, as discussed in greater detail below. Embodiments described herein also include physical and other computer-readable media for carrying or storing computer-executable instructions and/or data structures. Such computer-readable media can be any available media that can be accessed by a general purpose or special purpose computer system. Computer-readable media that store computer-executable instructions are physical storage media. Computer-readable media that carry computer-executable instructions are transmission media. Thus, by way of example, and not limitation, embodiments of the invention can comprise at least two distinctly different kinds of computer-readable media: computer storage media and transmission media.

Computer storage media includes RAM, ROM, EEPROM, CD-ROM or other optical disk storage, magnetic disk storage or other magnetic storage devices, or any other medium which can be used to store desired program code means in the form of computer-executable instructions or data structures and which can be accessed by a general purpose or special purpose computer.

Accordingly and in yet another embodiment, provided herein is a system for authenticating a bulk working liquid, the system comprising a fluorescence detector; a bulk liquid container; and a processing unit coupled to the fluorescence detector, with a processing module comprising a processor in communication with a linked library containing original emission spectra at a specific wavelength, excitation and emission contour map, absorption spectra, or their combination of a tagging carbon quantum dot incorporated in authentic liquid sought to be authenticated; the processor further being in communication with a non-volatile memory having thereon a processor-readable medium with a set of executable instructions configured to: receive a fluorescence reading from the fluorescence detector; retrieve from the linked library a predetermined emission spectra at a specific wavelength, excitation and emission contour map, absorption spectra, or their combination; and if the emission spectra at a specific wavelength, excitation and emission contour map, absorption spectra, or their combination, retrieved from the fluorescence detector correlates with the emission spectra at a specific wavelength, excitation and emission contour map, absorption spectra, or their combination, retrieved from the linked library, authenticating the tagged liquid; else identifying the liquid as non-authentic.

The term "module" is used herein to refer to software computer program code and/or any hardware or circuitry utilized to provide the functionality attributed to the module. Further, the term "module" or "component" can also refer to software objects or routines that execute on the computing system. The different components, modules, engines, and services described herein may be implemented as objects or processes that execute on the computing system (e.g., as separate threads).

Further, the CPM may be operably coupled to the various modules and components with appropriate circuitry. may also be used herein, the term(s) "operably coupled to", "coupled to", and/or "coupling" includes direct coupling between items and/or indirect coupling between items via an intervening item (e.g., an item includes, but is not limited to, a component, an element, a circuit, an engine, and/or a module) where, for indirect coupling, the intervening item does not modify the information of a signal but may adjust its current level, voltage level, and/or power level. As may further be used herein, inferred coupling (i.e., where one element is coupled to another element by inference) includes direct and indirect coupling between two items in the same manner as "coupled to". As may even further be used herein, the term "operable to" or "operably coupled to" indicates that an item includes one or more of power connections, input(s), output(s), etc., to perform, when activated, one or more its corresponding functions and may further include inferred coupling to one or more other items. As may still further be used herein, the term "associated with", includes direct and/or indirect coupling of separate items and/or one item being embedded within another item.

As may also be used herein, the terms "central processing module", "module", "processing circuit", and/or "processing unit" may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module, processing circuit, and/or processing unit may have an associated memory and/or an integrated memory element, which may be a single memory device, a plurality of memory devices, and/or embedded circuitry of the processing module, module, processing circuit, and/or processing unit. Such a memory device may be a read-only memory, random access memory, volatile memory, non-volatile memory, static memory, dynamic memory, flash memory, cache memory, and/or any device that stores digital information. Note that if the processing module, module, processing circuit, and/or processing unit includes more than one processing device, the processing devices may be centrally located (e.g., directly coupled together via a wired and/or wireless bus structure) or may be distributed (e.g., cloud computing via indirect coupling via a local area network and/or a wide area network). Further note that if the processing module, module, processing circuit, and/or processing unit implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element may store, and the processing module, module, processing circuit, and/or processing unit executes, hard coded and/or operational instructions corresponding to at least some of the steps and/or functions illustrated in one or more of the figures. Such a memory device or memory element can be included in an article of manufacture.

The systems compositions and methods described herein, can be used in various bulk liquids varying greatly in their apparent viscosity and degree of backgrounds luminescence and clarity. A nonexclusive list of potential implementations is provided in Table II below:

TABLE II

Applications

| Product | Composition | Viscosity at 25 C.° (cP) | Opacity |
|---|---|---|---|
| DEF | Water + urea | 0.6-0.9 | Clear & transparent |
| Inkjet ink - clear | Water + resin | 5-25 | Clear & transparent |
| Inkjet ink - pigmented | Water/MEK + resin + pigment | 10-50 | Color & Opaque |
| Varnishes | PVA and Acrylic resin | 500-2000 | Color & transparent Color & Opaque |
| Lubricants | Oils, hydrocarbon, silicone oil | 100-1000 | Color & transparent |
| Adhesives/Cast molds | Epoxy, polyurethane, silicone | 500-5000 | Clear & transparent |
| Concrete | Cement, eco polymer, fillers | 100-500 | Color & Opaque |

Table II illustrates that viscosity of the tagged liquid can vary between about 0.6 cP for Diesel Exhaust Fluid (e.g. AdBlue, DEF), to 5,000 cP for adhesives and varnishes. Likewise, the degrees of opacity referring to any change from transparency to opalescence, cloudiness, turbidity or precipitation, all which tend to obscure visual observation of a background viewed through the composition thus tending to make it opaque and no longer transparent.

The following examples are intended to illustrate but not limit the invention.

EXAMPLES

Example 1

Mixed PCNs in Diesel Exhaust Fluid

AdBlue™, an aqueous urea solution used as diesel exhaust fluid (DEF) was used to examine tagging using combination of various color PCNs and different concentrations. Accordingly, 60 ppb (w/w) of blue, 75 ppb (w/w) green, and 60 ppb blue with 71 ppb green PCNs were each separately incorporated into AdBlue™.

Figure 8A:
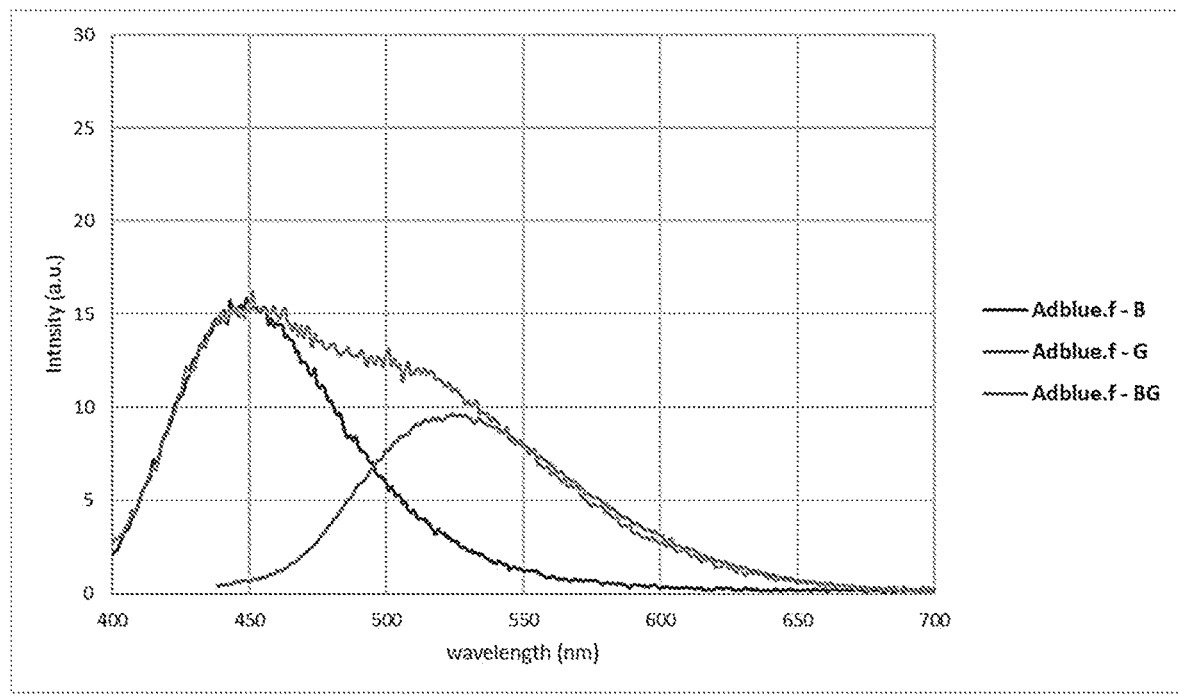
FIG. 8A shows photoluminescence (PL) spectra of low PCNs' concentration in AdBlue (Diesel Exhaust Fluid, DEF), with PL spectra of high PCNs' concentrations shown in FIG. 8B.

The emission spectra of the three solutions was measured using Agilent Cary Eclipse™ Fluorescence Spectrophotometer. Results are shown in FIG. 8. As illustrated, each color PCN shows a discrete emission peak corresponding to the maximum emission wavelength, with the blue PCNs exhibiting peak emission intensity at wavelength about 450 nm, green only PCN with peak emission intensity at about 530 nm and the solution with mixed PCNs (blue and green) showing a peak emission spectra, as described in FIG. 5B, that is a combination specific to the concentrations used. Higher concentrations (used for example, for non-forensic detection methods) were examined in the same fluid as well. Again, three separate solutions were prepared; a. 6 ppm blue PCNs, b. 7.5 ppm green PCNs, and a combination solution with 25 ppm blue PCNs and 30 ppm green PCNs.

Figure 8B:
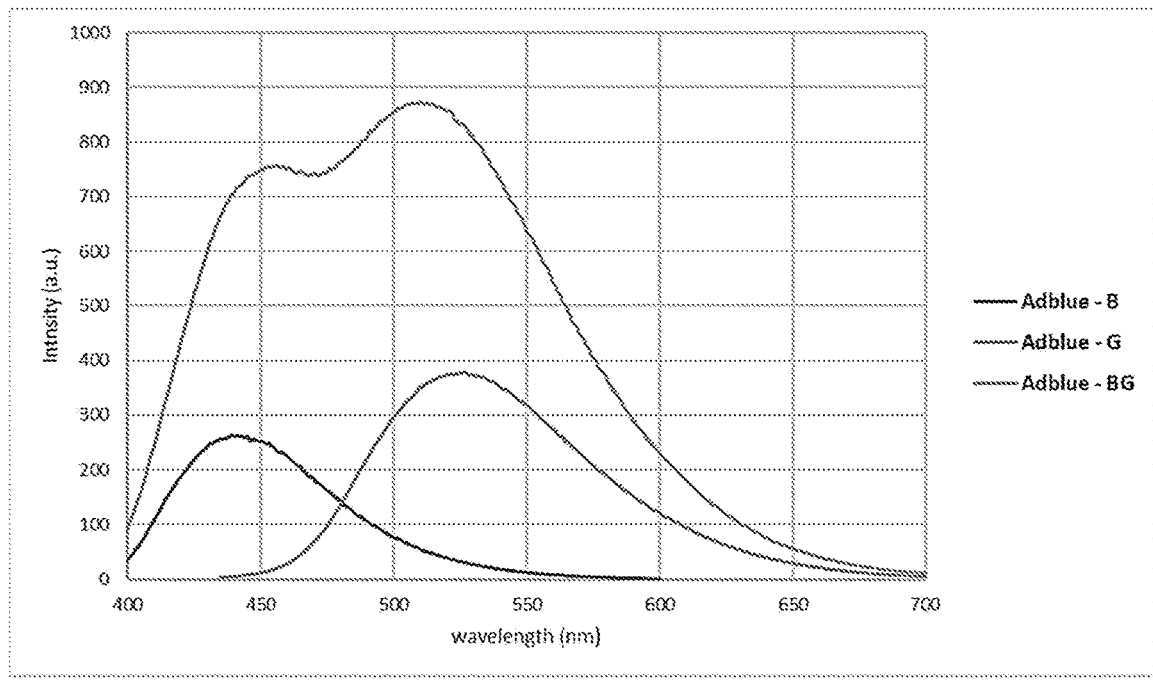

Results are shown in FIG. 8B, where emission spectra of the three solutions was again measured using Agilent Cary Eclipse™ Fluorescence Spectrophotometer. Again, each color PCN shows a discrete emission peak corresponding to the peak emission wavelength, with the blue PCNs exhibiting peak emission intensity at wavelength of about 440 nm, green only PCN with peak emission at about 530 nm and the solution with mixed PCNs (blue and green) showing an emission spectra, as described in FIG. 5B, that is a combination specific to the concentrations used. The mixed emission shows bimodal emission spectra, with one mode at 460 nm and a second mode at 520 nm. FIG. 8B shows that the peak emission intensity of the mixture is proportional to the PCN's concentration used.

Accordingly, storing the mixture's bimodal emission spectra can be used to authenticate the fluid's origin with high degree of specificity.

Example 2

Synthetic Motor Oil (Syntrax® 75W 140)

Syntrax 75W 140, is a synthetic axle oil with clear yellowish color. a mixture of violet and red PCNs were added. Three solutions of varying components were made. Violet alone (7.5 ppm), Red alone (1.5 ppm) and a mixture solutions. Results are shown in FIG. 9A. The results were obtained following baseline correction. As illustrated, the bimodal curve corresponds to the observed peak emission wavelength of each PCN color used alone and the baseline correction creates two discrete curves, the area of which (AUC) can be used to authenticate the sample.

Using the same oil, a different mixture of blue and red PCNs at different concentrations (1.5 ppm and 1.5 ppm for blue and red PCNs respectively). As illustrated, following baseline correction two discrete curves are observed. It is noted that depending on the PCN used, and the tinting dye or background luminescence of the liquid, intensity at peak emission may change following the baseline correction.

Example 3

PCNs in Concrete

Tagging of solid application was tested by incorporating blue PCNs to a concrete mixture containing dyed, substantially crystalline glass beads. In the procedure, 80 g of white cement and 80 g of crystalline, dyed glass beads (Jewels 4 Pools J4P) were mixed together. 20-40 ml of water and 2 ml of polymer additive (Geo Polymer®, Jewels 4 Pools), were mixed separately. Blue PCNs at various concentrations were added to the water and polymer additive. Prior to adding the PCNs solution, the water content in the liquid mixture with the polymer additive was reduced by the corresponding PCNs' solution volume. The liquid mixture was then admixed with the dry ingredients, at which point additional 80 g of the dyed glass beads were added to the suspension. The obtained Cementous mixture was poured into molds and left to cure for 24 hrs. Results are shown in FIGS. 10A-11.

Figure 10A:
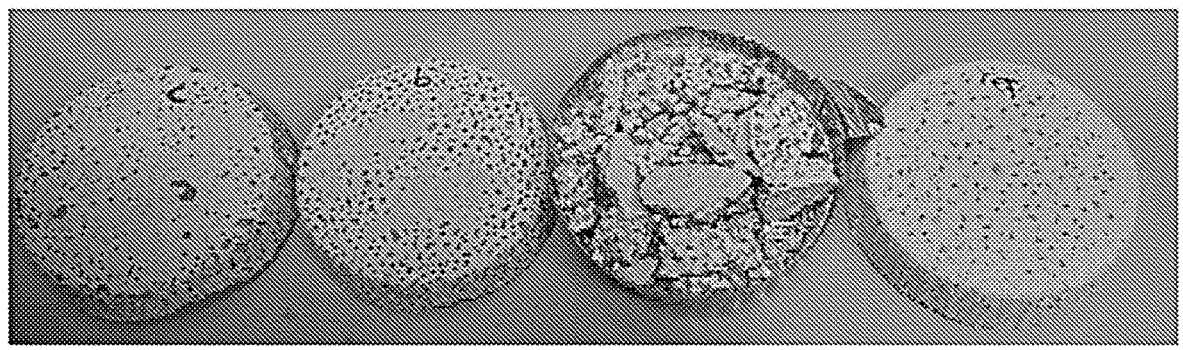
FIG. 10A illustrates cured concrete sample prepared using varying amounts of (blue) PCNs tagging under day light and under UV light in FIG. 10B.
Figure 11:
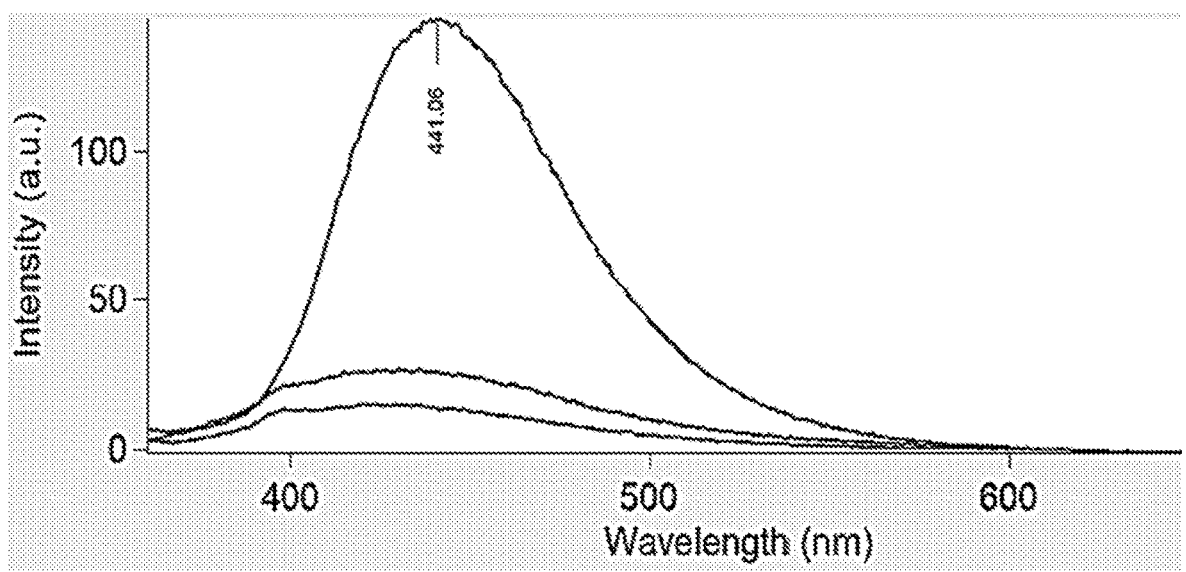
FIG. 11, shows PL intensity of PCNs extracted from crushed concrete.

Turning now to FIG. 10A, showing the molds after curing and attempting to remove the concrete pucks from the molds. From right to left the samples were:

The reference formulation without added PCNs;

5 ml (2000 ppm) of Blue PCN were added to 120 g concrete mixture (80 cement+40 g water). Results show the concrete as brittle and crumbled easily (couldn't be released from mold) (sample a);

2 ml (800 ppm) of Blue PCNs were added to 120 g concrete (80 cement+40 g water). Results show the concrete with good hardness and consistency, which didn't break when released from the mold (sample b); and 2 ml (920 ppm) of Blue PCNs were added to 104.5 g concrete (80 cement+24.5 g water (minimum quantity)). The mixture was very thick and hard to mix. The obtained cured concrete didn't break when released from the mold.

Figure 10B:
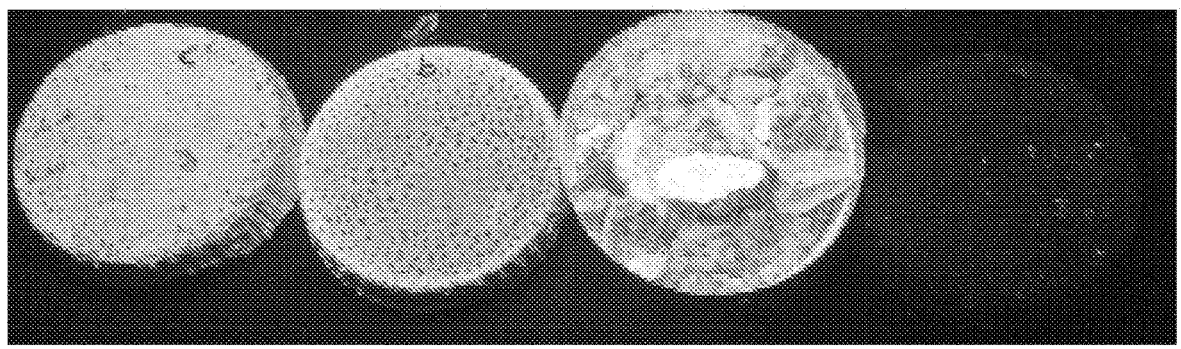

As illustrated in FIG. 10A, the concentration used are invisible to the naked eye under normal daylight. FIG. 10B shows the results when viewed under UV light. It is evident from FIG. 10B that the PCNs are dispersed uniformly throughout the solid concrete mixture without significant quenching; and that the concentrations used are all above the dynamic response range, indicating that the concentrations needed to tag the concrete mixture can be reduced.

Isolating the PCNs from the concrete mixture was done as follows: the concrete was crushed and immersed in hot water (50° C.) for about 1 hr. in order to extract the entrapped PCNs from the concrete. The extraction solution was filtered (0.2 μm filter) from the crushed concrete and concentrated by evaporation. The 100 ppm sample (See e.g., FIG. 11) was measured without concentrating the solution. Samples with calculated concentration of 1 ppm and 500 ppb were further concentrated in order to obtain detectable signal. As illustrated in FIG. 11, The PCNs were successfully extracted from the concrete and the PL was measured even at PCN concentration of 500 ppb. As shown, PL intensity was proportional to PCNs concentration. Namely, dilution of the polymer additive (e.g., Geo Polymer®) formulations with other non-tagged materials (by counterfeiters and adulterers) is detectable using the methods provided herein.

The terms "a", "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the network(s) includes one or more network). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The term "system" shall also be taken to include any collection of systems or sub-systems that individually or jointly execute a set, or multiple sets, of instructions to perform one or more functions. Also, the term "system" refers to a logical assembly arrangement of multiple devices, and is not restricted to an arrangement wherein all of the component devices are in the same housing.

In an embodiment therefore, provided herein is a method of tagging a liquid, comprising: providing a composition comprising photoluminescent carbon nanostructures (PCN's) suspended in a continuous phase having at least one of a limited solubility in the tagged liquid and substantially low concentration of PCNs; and incorporating the PCNs' suspension into the liquid, wherein the suspension is incorporated at a concentration of continuous phase that is at least one of being below the solubility limit of the suspension's continuous phase in the bulk liquid and a concentration that cannot be observed unaided to the naked eye, wherein (i) the PCNs are carbon nanotube quantum dots, graphene quantum dots, graphene oxide quantum dots or a combination of PCNs comprising one or more of the foregoing, (ii) wherein the tagged liquid is crude oil, fuel, olive oil or a non-polar bulk liquid, (iii) wherein the continuous phase is a polar liquid, (iv) wherein the tagged liquid is wine, (v) wherein PCNs are modified to form a non-polar surface, (vi) wherein the continuous phase is polar, (vii) wherein the step of incorporating comprises using a dosing pump in liquid communication with the tagged liquid, (viii) wherein the PCNs are of a single $D_{2,1}$ particle size average and (ix) wherein the PCNs comprise a mixture having a predefined $D_{2,1}$ particle size.

In another embodiment, provided herein is a method of identifying a tagged non-polar liquid, implementable in a tagged non-polar bulk liquid wherein the non-polar bulk liquid was tagged by incorporating a composition comprising PCNs suspended in a continuous phase having limited solubility in the tagged non-polar bulk liquid at a concentration of continuous phase that is below the solubility limit, the method comprising: obtaining a sample of predetermined volume from the non-polar bulk liquid; admixing into the non-polar bulk liquid the continuous phase of the suspension to a concentration above the solubility limit of the continuous phase in the tagged non-polar bulk liquid; partitioning the continuous phase from the tagged non-polar bulk liquid; exposing the continuous phase to an electromagnetic radiation source of at least one of a predefined wavelength, a predefined wavelength range, and a plurality of predefined wavelength range segments; and detecting at least one of: excitation/emission contour map, emission spectra, and absorption spectra of the partitioned continuous phase, (x) wherein the step of detecting comprises using a predetermined detection protocol, (xi) wherein the tagged liquid is crude oil, fuel, olive oil or a non-polar bulk liquid, (xii) wherein the continuous phase is a polar liquid, (xiii) wherein the tagged liquid is a synthetic engine oil, (xiv) wherein the PCNs are modified to form a non-polar surface, (xv) wherein the continuous phase is non-polar, (xvi) wherein the step of incorporating comprising using a dosing pump in liquid communication with the tagged non-polar bulk liquid, (xvii) wherein the PCNs are of a single $D_{2,1}$ particle size average, (xviii) wherein the PCNs comprise a mixture having a predefined $D_{2,1}$ particle size, (xix) wherein the PCNs have different peak emission wavelength, the method further comprising (xx) further comprising: comparing the detected emission spectra to a predetermined emission spectra corresponding to an authentic identity; and if the emission spectra correlates with the predetermined emission spectra, authenticating the tagged liquid; else identifying the liquid as non-authentic, (xxi) wherein, if the tagged non-polar bulk liquid is tinted with dye, further comprising a step of using baseline correction, subtracting background emission corresponding to the dye without the PCNs.

While particular embodiments have been described, alternatives, modifications, variations, improvements, and substantial equivalents that are or may be presently unforeseen may arise to applicants or others skilled in the art. Accordingly, the appended claims as filed and as they may be amended, are intended to embrace all such alternatives, modifications variations, improvements, and substantial equivalents.

The invention claimed is:

1. A method of identifying a tagged non-polar liquid, implementable in a tagged non-polar bulk liquid wherein the non-polar bulk liquid was tagged by incorporating a composition comprising PCNs suspended in a continuous phase having limited solubility in the tagged non-polar bulk liquid at a concentration of continuous phase that is below the solubility limit, the method comprising:
   a. obtaining a sample of predetermined volume from the non-polar bulk liquid;
   b. admixing into the non-polar bulk liquid the continuous phase of the suspension to a concentration above the solubility limit of the continuous phase in the tagged non-polar bulk liquid;
   c. partitioning the continuous phase from the tagged non-polar bulk liquid;
   d. exposing the continuous phase to an electromagnetic radiation source of at least one of a predefined wavelength, a predefined wavelength range, and a plurality of predefined wavelength range segments; and
   e. detecting at least one of: excitation/emission contour map, emission spectra, and absorption spectra of the partitioned continuous phase.

2. The method of claim 1, wherein the tagged liquid is selected from crude oil, synthetic engine oil, fuel, olive oil and a non-polar bulk liquid.

3. The method of claim 2, wherein the continuous phase is a polar liquid.

4. The method of claim 1, wherein the PCNs are modified to form a non-polar surface.

5. The method of claim 4, wherein the continuous phase is non-polar.

6. The method of claim 1, wherein the PCNs are of a single $D_{2,i}$ particle size average.

7. The method of claim 1, wherein the PCNs comprise a mixture having a predefined $D_{2,i}$ particle size.

8. The method of claim 7, wherein the PCNs have different peak emission wavelength.

9. The method of claim 1, further comprising:
   a. comparing the detected emission spectra to a predetermined emission spectra corresponding to an authentic identity; and
   b. if the emission spectra correlates with the predetermined emission spectra, authenticating the tagged liquid; else
   c. identifying the liquid as non-authentic.

10. The method of claim 9, wherein, if the tagged non-polar bulk liquid is tinted with dye, further comprising a step of using baseline correction, subtracting background emission corresponding to the dye without the PCNs.

* * * * *